US012036054B2

(12) United States Patent
Imai et al.

(10) Patent No.: US 12,036,054 B2
(45) Date of Patent: Jul. 16, 2024

(54) IMAGED-RANGE DEFINING APPARATUS, MEDICAL APPARATUS, AND PROGRAM

(71) Applicant: GE Precision Healthcare LLC, Wauwatosa, WI (US)

(72) Inventors: Yasuhiro Imai, Tokyo (JP); Yoshihiro Oda, Tokyo (JP); Ayako Matsumi, Tokyo (JP)

(73) Assignee: GE Precision Healthcare LLC, Wauwatosa, WI (US)

( * ) Notice: Subject to any disclaimer, the term of this patent is extended or adjusted under 35 U.S.C. 154(b) by 0 days.

(21) Appl. No.: 18/308,369

(22) Filed: Apr. 27, 2023

(65) Prior Publication Data

US 2023/0263485 A1 Aug. 24, 2023

Related U.S. Application Data

(62) Division of application No. 17/211,271, filed on Mar. 24, 2021, now Pat. No. 11,672,494.

(30) Foreign Application Priority Data

Mar. 31, 2020 (JP) .................................. 2020-063111

(51) Int. Cl.
*A61B 6/04* (2006.01)
*A61B 6/03* (2006.01)
(52) U.S. Cl.
CPC ............ *A61B 6/0492* (2013.01); *A61B 6/032* (2013.01); *A61B 6/0407* (2013.01)

(58) Field of Classification Search
CPC ..... A61B 5/064; A61B 5/0037; A61B 5/1127; A61B 3/0041; A61B 3/0058; A61B 5/0059; A61B 8/5238; A61B 8/5246; A61B 8/5292; A61B 8/462; A61B 8/5207; A61B 6/025; A61B 6/032; G16H 30/20; G01N 2021/6423
See application file for complete search history.

(56) References Cited

FOREIGN PATENT DOCUMENTS

JP 2021137259 A * 9/2021

* cited by examiner

*Primary Examiner* — Don K Wong

(57) ABSTRACT

The present disclosure relates to a system and method with which an imaged range in the past can be reproduced with high precision. In accordance with certain embodiments, an X-ray CT apparatus includes a camera-image producing section for producing a first camera image of a patient, a landmark fixing section for fixing a landmark with reference to a chest of the patient, and an imaged-range defining section for defining a first imaged range in a first scan based on landmark data representing the landmark. The camera-image producing section acquires a second camera image of the patient in a follow-up examination, the landmark fixing section fixes a second landmark with reference to the chest of the patient contained in the second image, and the imaged-range defining section defines second imaged range in a second scan based on landmark data representing the landmarks, and imaged-range data representing the first imaged range.

11 Claims, 23 Drawing Sheets

IMAGED-RANGE DEFINING APPARATUS, MEDICAL APPARATUS, AND PROGRAM

CROSS-REFERENCE TO RELATED APPLICATIONS

This application is a divisional of U.S. application Ser. No. 17/211,271, filed on Mar. 24, 2021, which claims priority to Japanese Application No. 2020-063111, filed on Mar. 31, 2020, the disclosure of which is incorporated herein by reference in its entirety.

FIELD

The present disclosure relates to an imaged-range defining apparatus for defining an imaged range in a patient, a medical apparatus having the imaged-range defining apparatus, and a program applied to the imaged-range defining apparatus.

BACKGROUND

X-ray CT apparatuses are known as medical apparatuses for non-invasively capturing an image of the inside of a patient's body. Since X-ray CT apparatuses are capable of imaging a body part to be imaged in a short duration, they are widely used in medical institutions, such as hospitals.

CT images obtained by imaging a patient by an X-ray CT apparatus are saved in a system such as a PACS. A physician then performs radiographic interpretation on the saved CT images to make a diagnosis based on a result of the radiographic interpretation.

When it is decided as a result of the diagnosis on a patient that subsequent observation of the patient's condition is needed, for example, the patient sometimes undergoes a follow-up examination at some later date.

In the follow-up examination, it is important to perform a scan on the same imaged range as that defined in the previous (past) examination. Therefore, in performing the follow-up examination, a radiologic technologist defines an imaged range in the follow-up so that it matches the imaged range in the examination in the past as much as possible while referring to images captured in the past, imaging conditions for the images in the past, and/or the like.

There is, however, a problem that it is difficult for the radiologic technologist who manually defines an imaged range to reproduce the imaged range in the past with good precision. Moreover, there is another problem that variability in a defined imaged range across individual radiologic technologists is encountered.

Therefore, there is a need for a technique with which an imaged range in the past can be reproduced with good precision.

BRIEF SUMMARY

This summary introduces concepts that are described in more detail in the detailed description. It should not be used to identify essential features of the claimed subject matter, nor to limit the scope of the claimed subject matter.

The present disclosure, in its first aspect, is an imaged-range defining apparatus of a medical apparatus for acquiring a medical image of a patient. The imaged-range defining apparatus includes a camera-image producing section for producing a first camera image containing an external appearance of the patient lying on a table in a first examination of the patient. The imaged-range defining apparatus further includes a landmark fixing section for fixing a first landmark with reference to a body part to be imaged of the patient contained in the first camera image. The imaged-range defining apparatus also includes an imaged-range defining section for defining a first imaged range in the patient in a first scan performed in the first examination based on first landmark data representing the first landmark. The camera-image producing section produces a second camera image containing the external appearance of the patient lying on a table in a second examination performed after the first examination. The landmark fixing section fixes a second landmark with reference to the body part to be imaged of the patient contained in the second camera image. The imaged-range defining section defines a second imaged range in the patient in a second scan performed in the second examination based on the first landmark data, second landmark data representing the second landmark, and imaged-range data representing the first imaged range.

The present disclosure, in its second aspect is a medical apparatus for acquiring a medical image of a patient. The medical apparatus includes a camera-image producing section for producing a first camera image containing an external appearance of the patient lying on a table in a first examination of the patient. The medical apparatus further includes a landmark fixing section for fixing a first landmark with reference to a body part to be imaged of the patient contained in the first camera image. The medical apparatus also includes an imaged-range defining section for defining a first imaged range in the patient in a first scan performed in the first examination based on first landmark data representing the first landmark. The camera-image producing section produces a second camera image containing the external appearance of the patient lying on a table in a second examination performed after the first examination. The landmark fixing section fixes a second landmark with reference to the body part to be imaged of the patient contained in the second camera image. The imaged-range defining section defines a second imaged range in the patient in a second scan performed in the second examination based on the first landmark data, second landmark data representing the second landmark, and imaged-range data representing the first imaged range.

The present disclosure, in its third aspect is a program applied to an imaged-range defining apparatus of a medical apparatus for acquiring a medical image of a patient. The program causes a processor to execute camera-image producing processing of producing a first camera image containing an external appearance of the patient lying on a table in a first examination of the patient. The program further causes the processor to execute landmark fixing processing of fixing a first landmark with reference to a body part to be imaged of the patient contained in the first camera image. The program also causes the processor to execute imaged-range defining processing of defining a first imaged range in the patient in a first scan performed in the first examination based on first landmark data representing the first landmark. The camera-image producing processing comprises processing of producing a second camera image containing the external appearance of the patient lying on a table in a second examination performed after the first examination. The landmark fixing processing comprises processing of fixing a second landmark with reference to the body part to be imaged of the patient contained in the second camera image. The imaged-range defining processing comprises processing of defining a second imaged range in the patient in a second scan performed in the second examination based on the first landmark data, second landmark data representing the second landmark, and imaged-range data representing the first imaged range.

The present disclosure, in its fourth aspect, is a non-transitory, computer-readable recording medium in which one or more processor-executable instructions are stored. The one or more instructions causing, when executed by the processor, the processor to execute an operation comprising the steps of producing a first camera image containing an external appearance of the patient lying on a table in a first examination of the patient, fixing a first landmark with reference to a body part to be imaged of the patient contained in the first camera image, defining a first imaged range in the patient in a first scan performed in the first examination based on first landmark data representing the first landmark, producing a second camera image containing the external appearance of the patient lying on a table in a second examination performed after the first examination, fixing a second landmark with reference to the body part to be imaged of the patient contained in the second camera image, and defining a second imaged range in the patient in a second scan performed in the second examination based on the first landmark data, second landmark data representing the second landmark, and imaged-range data representing the first imaged range.

A first landmark is fixed based on a first camera image acquired in a first examination, and a first imaged range in the first examination is defined based on the first landmark. In a second examination, a second imaged range is defined based on the first landmark and the first imaged range obtained in the first examination. Since substantially the same range as the imaged range in the first examination can thus be defined as the imaged range in the second examination, it is possible to reproduce the imaged range in the past with good precision.

DETAILED DESCRIPTION

Embodiments of the present disclosure will now be described, by way of example, with reference to the Figures, and the present disclosure is not limited thereto.

Figure 1:
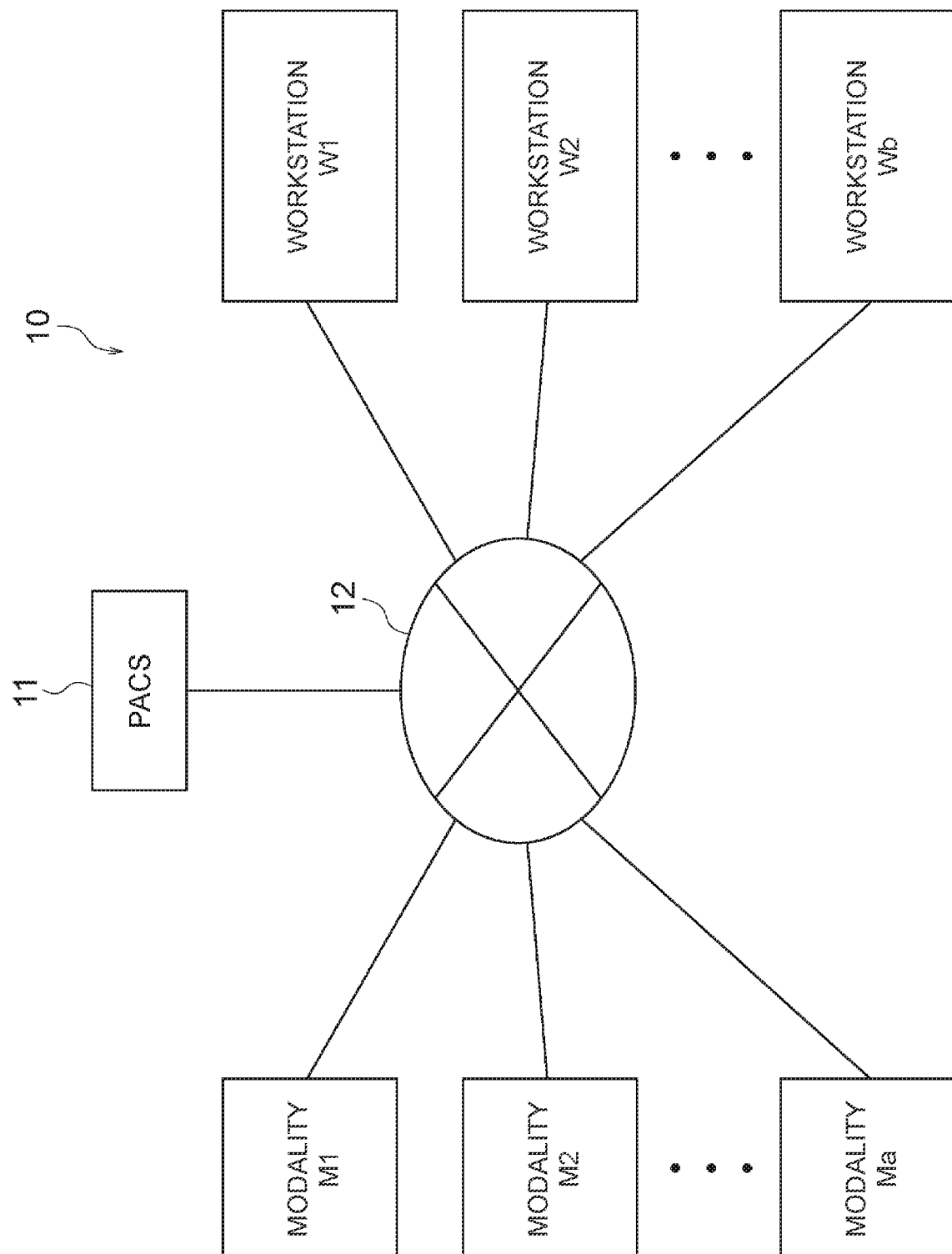
FIG. 1 is a diagram showing a medical information management system 10 comprising a medical apparatus in one embodiment of the present disclosure.

FIG. 1 is a diagram showing a medical information management system 10 comprising a medical apparatus in one embodiment of the present disclosure.

The system 10 comprises a plurality of modalities M1 to Ma. The plurality of modalities M1 to Ma include radiation-based ones performing diagnosis, treatment, and/or the like on a patient, such as an X-ray CT apparatus and a PET-CT apparatus, and non-radiation-based ones performing diagnosis, etc. on a patient, such as an MRI apparatus.

The system 10 also has a PACS (Picture Archiving and Communication System) 11. The PACS 11 receives data of images, etc. obtained in the modalities via a communication network 12, and archives the received data. The PACS 11 also transfers the archived data via the communication network 12, as needed.

The system 10 further has a plurality of workstations W1 to Wb. These workstations W1 to Wb are, for example, those used in a hospital information system (HIS), a radiology information system (RIS), a clinical information system (CIS), a cardiovascular information system (CVIS), a library information system (LIS), an electronic medical record (EMR) system, and/or any other image and information management system, etc., and those used in image inspection works by radiologists.

The system 10 is thus constructed as above. Next, an example of a configuration of an X-ray CT apparatus, which is an example of the modalities, will be described.

Figure 2:
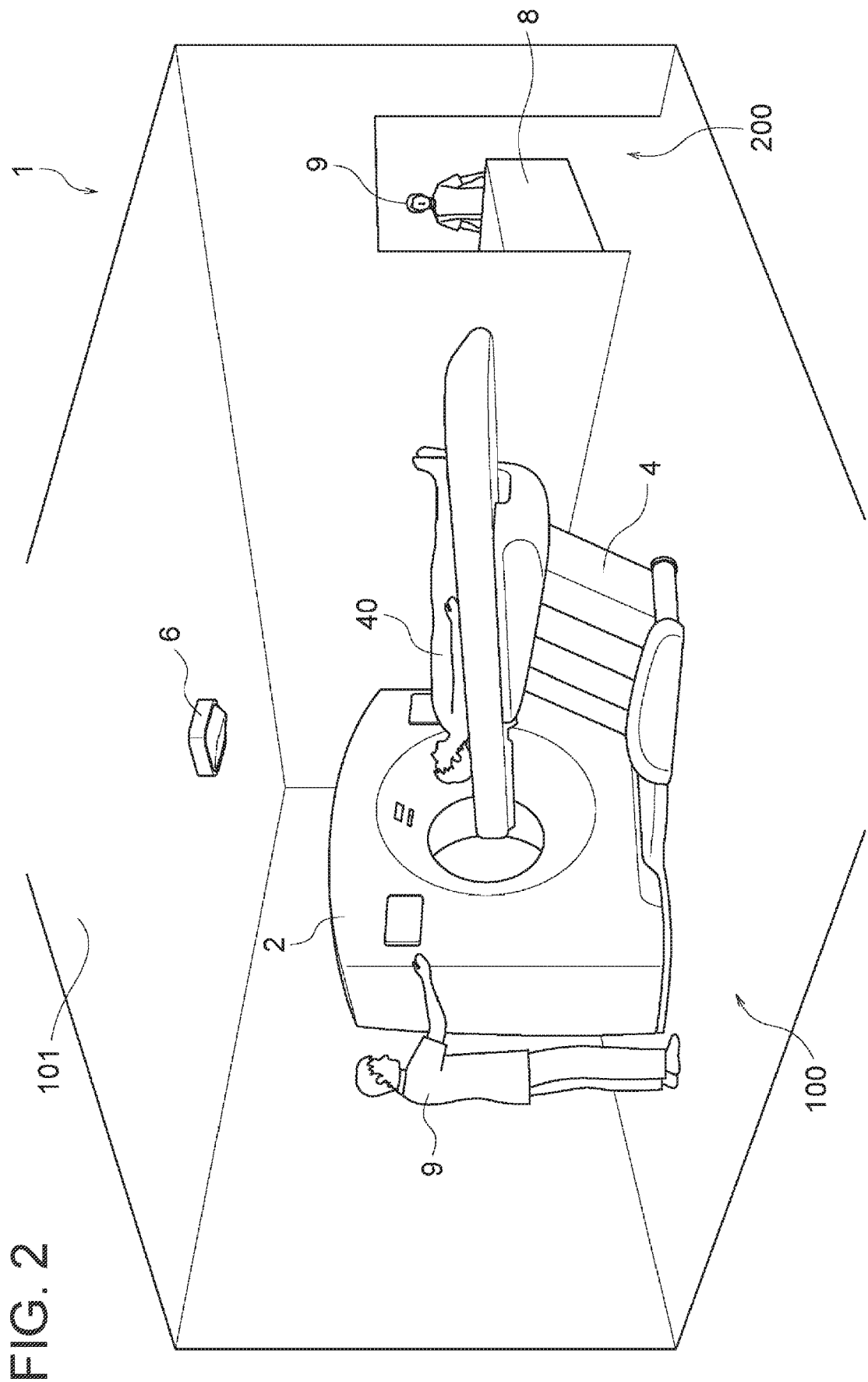
FIG. 2 is a schematic view of an X-ray CT apparatus.

FIG. 2 is a schematic view of an X-ray CT apparatus.

As shown in FIG. 2, an X-ray CT apparatus 1 comprises a gantry 2, a table 4, a camera 6, and an operator console 8.

The gantry 2 and table 4 are installed in a scan room 100. The camera 6 is installed in a ceiling 101 of the scan room 100. The operator console 8 is installed in an operation room 200.

Figure 3:
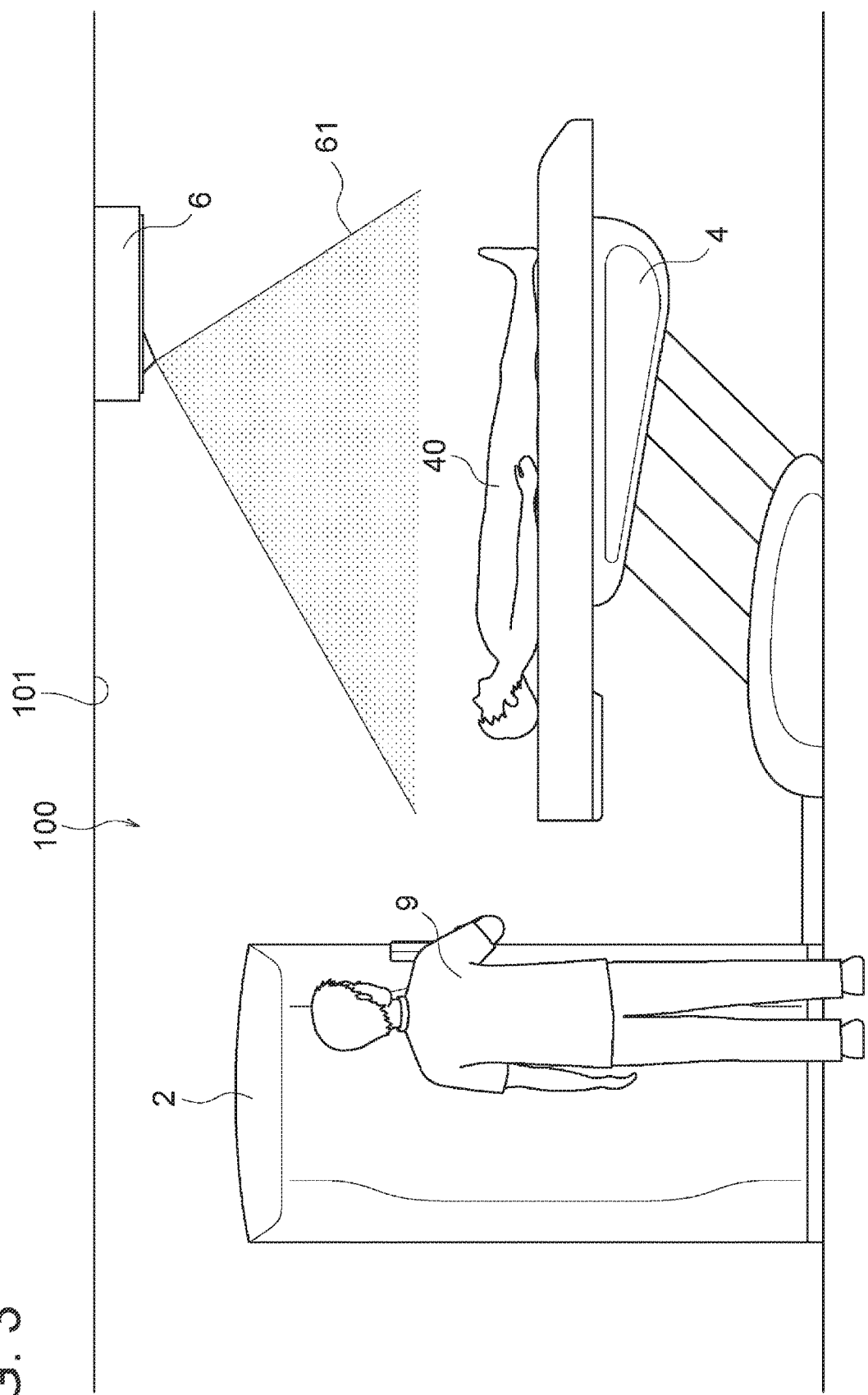
FIG. 3 is a side view of a gantry 2 and a table 4 installed in a scan room 100.
Figure 4:
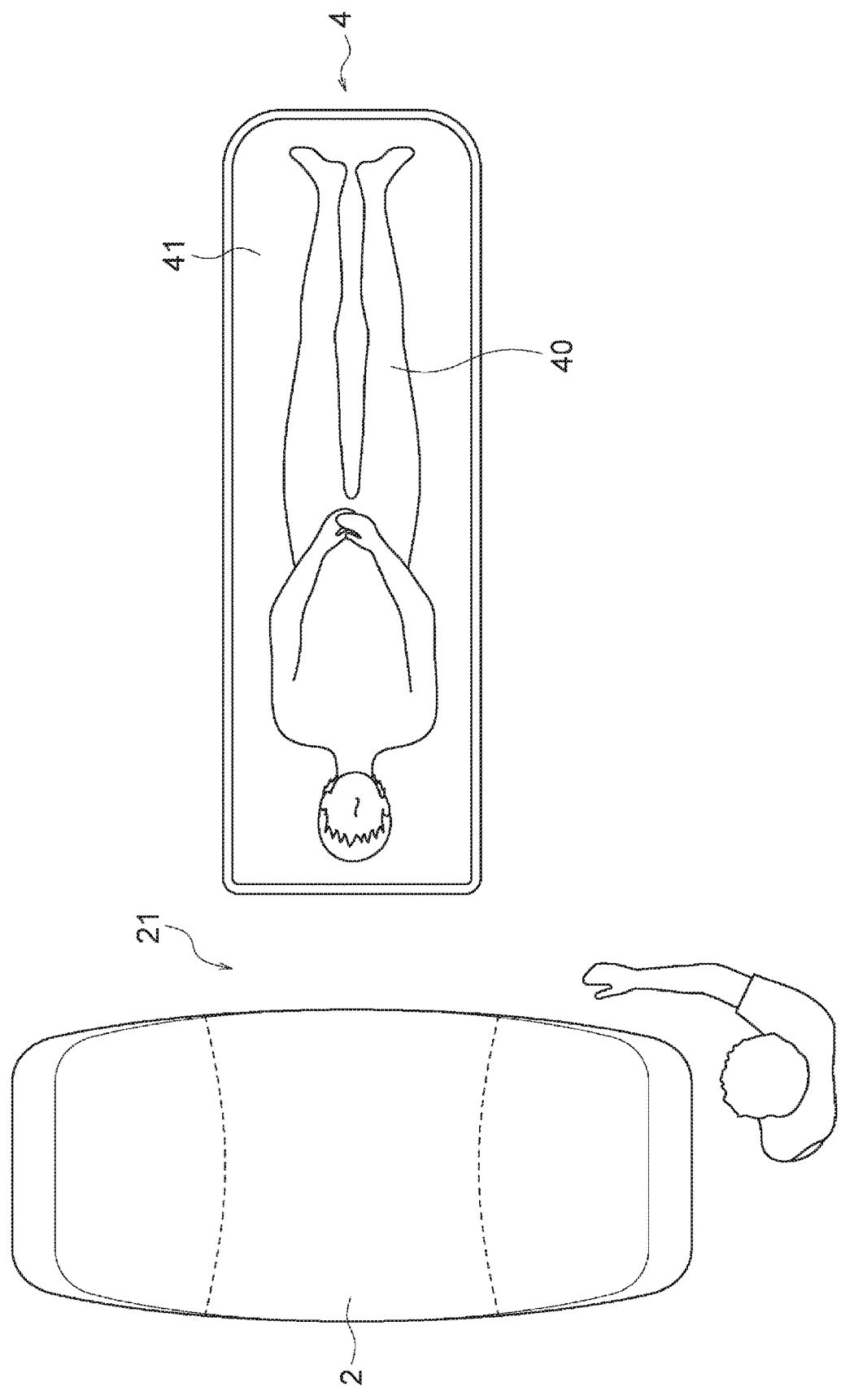
FIG. 4 is a top plan view of the gantry 2 and table 4 installed in the scan room 100.

FIG. 3 is a side view of the gantry 2 and table 4 installed in the scan room 100, and FIG. 4 is a top plan view thereof. In FIG. 3 is also shown the camera 6 installed in the ceiling 101 of the scan room 100.

The camera 6 is installed in a portion of the ceiling 101 facing the table 4. An imaging field of view 61 of the camera 6 is set to include the table 4 and its surrounding region. The camera 6 has imaging elements, and light detected by the imaging elements is converted into electrical signals, which are output to the operator console 8 (see FIG. 1). A processing apparatus 84 (see FIG. 5) in the operator console 8 produces a camera image based on the signals received from the camera 6.

According to the present embodiment, a camera capable of capturing a video is used as the camera 6. In the present disclosure, however, the camera 6 is not limited to that capturing a video, and it may be a digital still camera for capturing a still image. Moreover, the camera 6 may be one for acquiring a monochrome camera image or one for acquiring a color camera image.

The light detected by the imaging elements in the camera 6 include infrared and ultraviolet light, etc., in addition to visible light. For the imaging elements, a CCD (Charge-Coupled Device) or a CMOS (Complementary MOS) may be used, for example. Moreover, as used in the present disclosure, a term 'camera image' refers to any image containing an external appearance of a patient. Therefore, the camera 6 for imaging the patient is not limited to the one having imaging elements detecting light, and a variety of cameras, such as an ultrasonic camera using ultrasound to acquire an image, may be used insofar as they can acquire such a camera image.

Furthermore, according to the present embodiment, the X-ray CT apparatus comprises one camera 6; however, it may comprise a plurality of cameras 6.

Next, the gantry 2, table 4, and operator console 8 will be described referring to the block diagram in FIG. 5.

Figure 5:
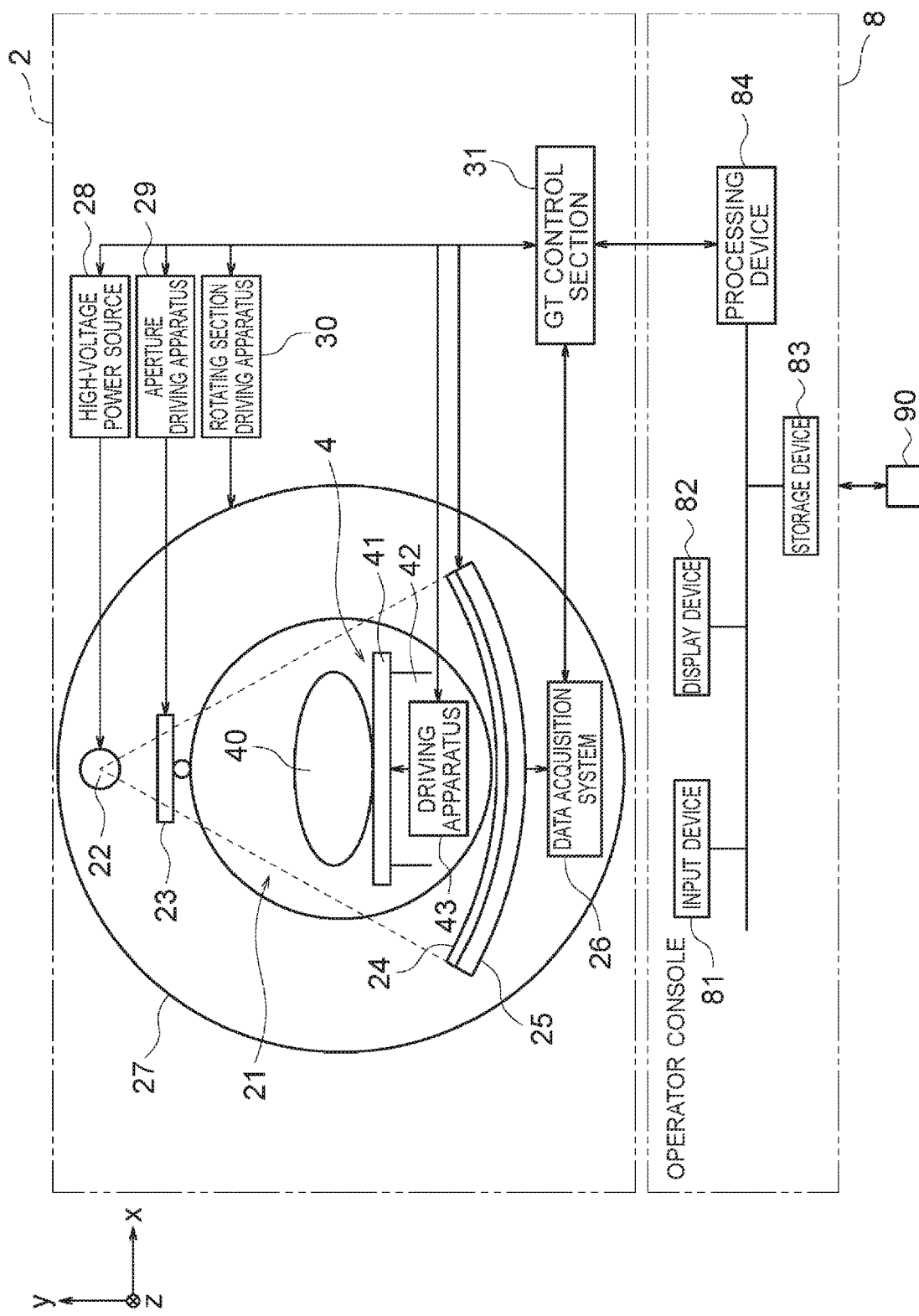
FIG. 5 is an explanatory diagram of the gantry 2, table 4, and an operator console 8.

FIG. 5 is an explanatory diagram of the gantry 2, table 4, and operator console 8.

The gantry 2 has a bore 21 for forming space through which a patient 40 can be moved.

The gantry 2 also has an X-ray tube 22, an aperture 23, a collimator 24, an X-ray detector 25, a data acquisition system 26, a rotating section 27, a high-voltage power source 28, an aperture driving apparatus 29, a rotating section driving apparatus 30, a GT (Gantry Table) control section 31, etc.

The X-ray tube 22, aperture 23, collimator 24, X-ray detector 25, and data acquisition system 26 are mounted on the rotating section 27.

The X-ray tube 22 and X-ray detector 25 are disposed facing each other sandwiching the bore 21 of the gantry 2.

The aperture 23 is disposed between the X-ray tube 22 and bore 21. The aperture 23 shapes X-rays emitted from an X-ray focus of the X-ray tube 22 toward the X-ray detector 25 into a fan beam or a cone beam.

The X-ray detector 25 detects X-rays passing through the patient 40.

The collimator 24 is disposed on a side of X-ray entrance with respect to the X-ray detector 25, for removing scattered X-rays.

The high-voltage power source 28 supplies high voltage and electric current to the X-ray tube 22.

The aperture driving apparatus 29 drives the aperture 23 to modify the shape of its opening.

The rotating section driving apparatus 30 rotationally drives the rotating section 27.

The table 4 has a cradle 41, a cradle support base 42, and a driving apparatus 43. The cradle 41 is for supporting the patient 40 that is an object to be imaged. The cradle support base 42 is for supporting the cradle 41 movably in y- and z-directions. The driving apparatus 43 is for driving the cradle 41 and cradle support base 42. Here, a direction of a body axis of the patient 40 is defined as the z-direction, a vertical direction as the y-direction, and a horizontal direction perpendicular to the z- and y-directions as an x-direction.

The GT control section 31 controls several apparatuses and sections in the gantry 2, the driving apparatus 43 for the table 4, etc.

The operator console 8 has an input device 81, a display device 82, a storage device 83, a processing apparatus 84, etc.

The input device 81 comprises a keyboard and a pointing device, etc. for accepting an input of a command and/or information from a radiologic technologist, and performing several kinds of operations. The display device 82 is for displaying visual information including images, etc., and is, for example, an LCD (Liquid Crystal Display), an organic EL (Electro-Luminescence) display, or the like.

In the storage device 83 are stored programs for executing several kinds of processing by the processor. The storage device 83 also stores therein several kinds of data, several kinds of files, etc. The storage device 83 has an HDD (Hard Disk Drive), DRAM (Dynamic Random Access Memory), ROM (Read Only Memory), etc. The storage device 83 may include a portable storage medium 90, such as a CD (Compact Disk) and a DVD (Digital Versatile Disk).

The processing apparatus 84 executes image reconstruction processing based on data for the patient 40 acquired with the gantry 2, and several other kinds of computations. The processing apparatus 84 has one or more processors, which execute several kinds of processing corresponding to the programs stored in the storage device 83. The processing apparatus 84 represents an example of the imaged-range defining apparatus.

The X-ray CT apparatus 1 is thus configured as above.

By using the X-ray CT apparatus 1, a CT image of the patient 40 can be acquired. A physician makes a diagnosis on the patient 40 based on the acquired CT images, and as a result of the diagnosis, she or he sometimes decides that subsequent observation of the patient's condition is needed. In this case, the patient 40 sometimes undergoes a follow-up examination at some later date, as needed.

In the follow-up examination, it is important to perform a scan on the same imaged range as that defined in the previous (past) examination. There is, however, a problem that it is difficult for the radiologic technologist to manually reproduce an imaged range defined in the previous (past) examination. Accordingly, the X-ray CT apparatus 1 is configured to reproduce the imaged range defined in the previous (past) examination with good precision. Now functions that the X-ray CT apparatus 1 has for reproducing the imaged range defined in the previous (past) examination with good precision will be described hereinbelow (see FIG. 6).

Figure 6:
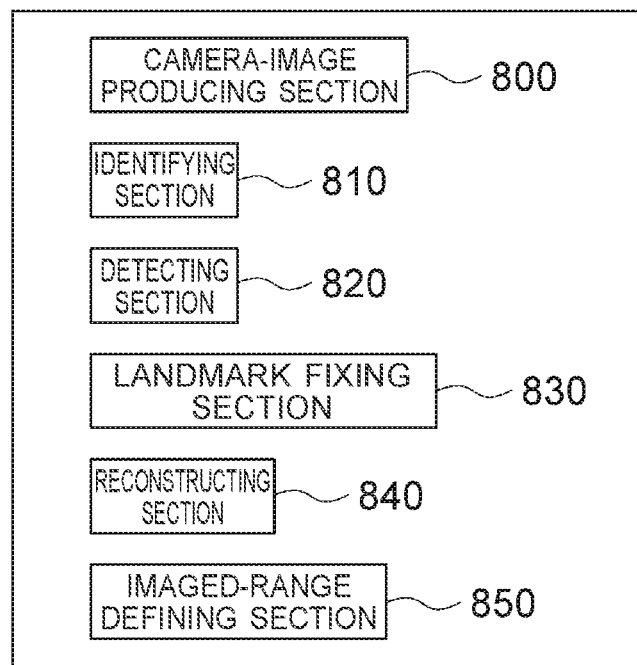
FIG. 6 is a block diagram of functions of the X-ray CT apparatus.

FIG. 6 is a block diagram of functions of the X-ray CT apparatus.

The X-ray CT apparatus is configured to execute the functions 800 to 850 below.

A camera-image producing section 800 executes the processing of producing a camera image based on signals received from the camera 6. When the patient 40 is lying on the table 4, the camera-image producing section 800 produces a camera image containing an external appearance of the patient 40 lying on the table 4 based on the signals received from the camera 6.

An identifying section 810 executes the processing of identifying the camera image containing the patient lying on the table in a predetermined posture from among a series of camera images produced by the camera-image producing section 800.

The detecting section 820 executes the processing of detecting a body part to be imaged of the patient from within the camera image identified by the identifying section 810.

A landmark fixing section 830 executes the processing of fixing a landmark with reference to the body part to be imaged detected by the detecting section 820.

A reconstructing section 840 executes the processing of reconstructing a CT image of the patient based on data collected by scanning the patient.

An imaged-range defining section 850 executes the processing of defining an imaged range in the patient 40 based on landmark data representing the landmark. When a follow-up examination is performed, the imaged-range defining section 850 defines an imaged range in a scan performed in the follow-up examination based on the landmark data representing the landmark fixed in the examination in the past, imaged-range data representing the imaged range in the scan performed in the examination in the past, and landmark data representing the landmark fixed in the follow-up examination. A detailed description of the method of defining the imaged range will be given later.

In the storage device 83 are stored programs representing the processing of the functional blocks described above. The storage device 83 may be a non-transitory, computer-readable recording medium in which one or more processor-executable instructions are stored. The one or more instructions cause, when executed by the processor, execution of the operation comprising the steps (a)-(f) below:

(a) producing a camera image containing an external appearance of the patient 40 lying on the table 4 based on signals received from the camera 6 (the camera-image producing section 800);

(b) identifying a camera image that contains the patient lying on the table in a predetermined posture from among a series of camera images produced by the camera-image producing section 800 (the identifying section 810);

(c) detecting a body part to be imaged of the patient from within the camera image identified by the identifying section 810 (the detecting section 820);

(d) fixing a landmark with reference to the body part to be imaged detected by the detecting section 820 (the landmark fixing section 830);

(e) reconstructing a CT image of the patient based on data collected by scanning the patient (the reconstructing section 840); and (f) defining an imaged range in the patient 40 based on landmark data representing the landmark, wherein when a follow-up examination is performed, an imaged range in a scan performed in the follow-up examination is defined based on the landmark data representing the landmark fixed in the examination in the past, imaged-range data representing the imaged range in the scan performed in the examination in the past, and landmark data representing the landmark fixed in the follow-up examination (the imaged-range defining section 850).

The operator console 8 comprises a non-transitory, computer-readable recording medium in which one or more instructions for executing the steps (a)-(f) are stored, and a processor for executing the instructions stored in the recording medium.

Note that in place of the processor in the processing apparatus 84, a processor in another apparatus (for example, the display device) in the operator console 8 may execute the functional blocks described above. For example, a processor provided in the camera 6 may execute the function (processing) of the camera-image producing section 800. Moreover, a processor included in the gantry 2 or table 4 may be caused to execute all or part of the processing of the functional blocks described above. Furthermore, it is possible to cause a processor included in another apparatus (for example, a workstation) different from the X-ray CT apparatus 1 to execute all or part of the processing of the functional blocks described above.

The system 10 comprises the thus-configured X-ray CT apparatus 1.

As described above, the X-ray CT apparatus 1 is configured to be capable of reproducing the imaged range defined in the previous (past) examination with good precision in performing the follow-up examination. Now a method of reproducing an imaged range defined in a previous (past) examination in the present embodiment will be described hereinbelow. The following description will be made taking an example in which an initial examination (first examination) is performed on the patient 40, and an imaged range is defined when performing a follow-up examination (second examination) at some later date, as an example of the method of reproducing an imaged range. First, the flow in performing the first examination of the patient 40 will be described referring to FIG. 7.

Referring to the first examination, at Step ST1, the radiologic technologist 9 calls the patient 40 into the scan room 100, and lays the patient 40 on the table 4, as shown in FIGS. 2 to 4. The radiologic technologist 9 also sets imaging conditions (for example, tube voltage, tube current, exposure time) for the patient 40.

Note that the camera 6 has started imaging of the table 4 and its surrounding region since before the patient 40 enters the scan room 100. Signals acquired by the camera 6 are sent to the processing apparatus 84 in the operator console 8. The processing apparatus 84 produces a camera image based on the signals received from the camera 6. Therefore, a camera image of an imaged object within the imaging field of view 61 can be produced from before the patient 40 enters the scan room 100. The processing apparatus 84 executes the processing of producing a camera image by the camera-image producing section 800 (see FIG. 6).

The imaging field of view 61 of the camera 6 contains the table 4 and its surrounding region. Therefore, once the patient 40 has lain on the table 4 (cradle 41), the camera-image producing section 800 can produce a camera image containing an external appearance of the patient 40 lying on the table 4 (cradle 41) based on the signals from the camera 6. The camera image is stored in the storage device 83. After laying the patient 40 on the cradle 41, the flow goes to Step ST2.

At Step ST2, the processor in the processing apparatus 84 executes the processing of fixing a landmark based on the camera image produced by the camera-image producing section 800. Now a landmark fixing method will be described hereinbelow (see FIGS. 8 to 11).

FIGS. 8 to 11 are explanatory diagrams for the landmark fixing method.

Figure 8:
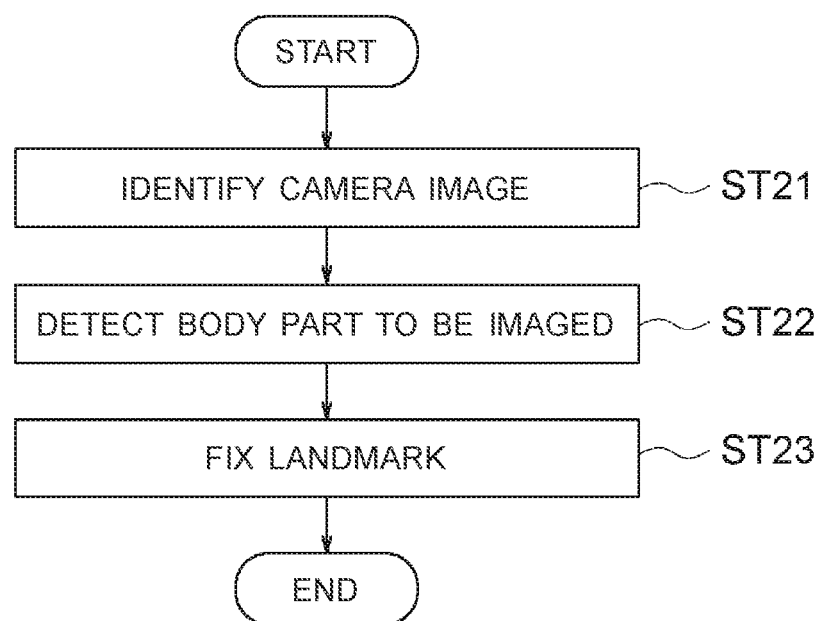
FIG. 8 is a chart showing an example of flow of a landmark fixing method.

FIG. 8 is a chart showing an example of flow of the landmark fixing method.

At Step ST21, the processor in the processing apparatus 84 executes the processing of identifying a camera image 50 containing the patient 40 lying on the table 4 in a posture suitable for imaging from among a series of camera images produced by the camera-image producing section 800. The processor in the processing apparatus 84 executes the processing of identifying the camera image by the identifying section 810 (see FIG. 6). As the identifying method, the following identifying methods 1 to 3 may be contemplated, for example.

Figure 9:
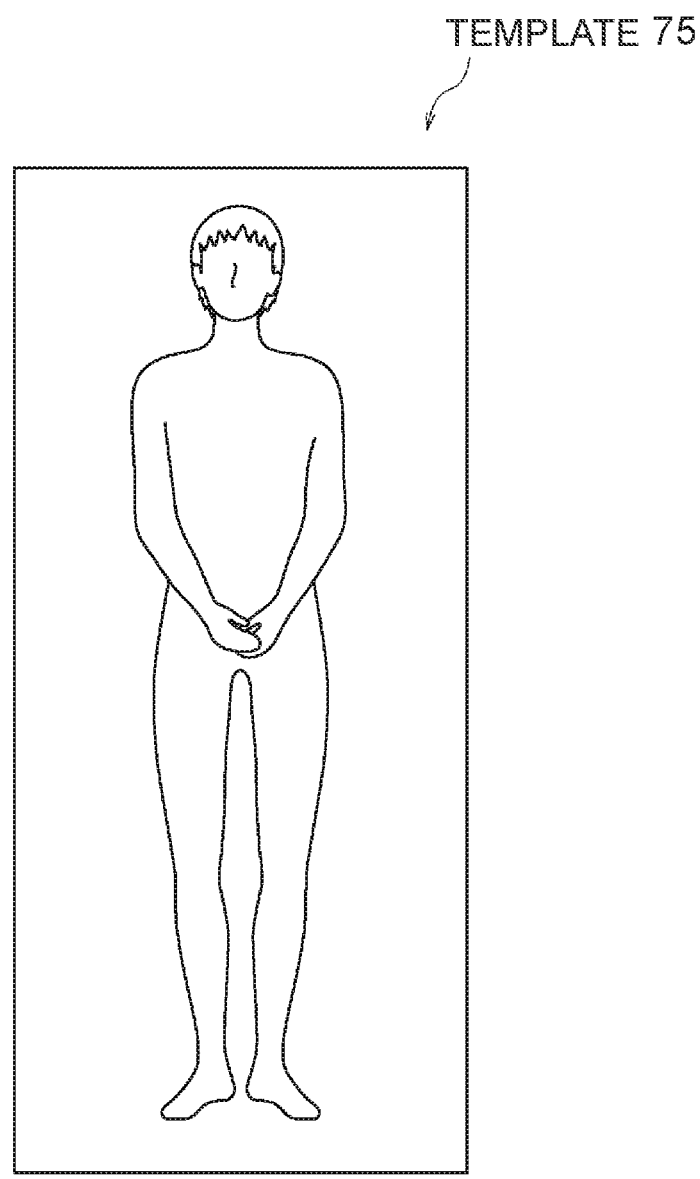
FIG. 9 is a diagram schematically showing an example of a standard human posture represented by a template 75.

Referring to Method 1, templates representing standard postures of a human being lying on the table 4 are stored in the storage device 83 beforehand. FIG. 9 schematically shows an example of the standard human posture that a template 75 represents. For convenience of explanation, a posture with the hands laid on the abdomen and legs naturally stretched is assumed as the standard human posture on the table 4. The standard posture is, however, not limited to the one with the hands laid on the abdomen and legs naturally stretched, and various postures are possible according to the kind of examination, including, for example, a posture with the legs bending at the knees at a certain angle.

Figure 10:
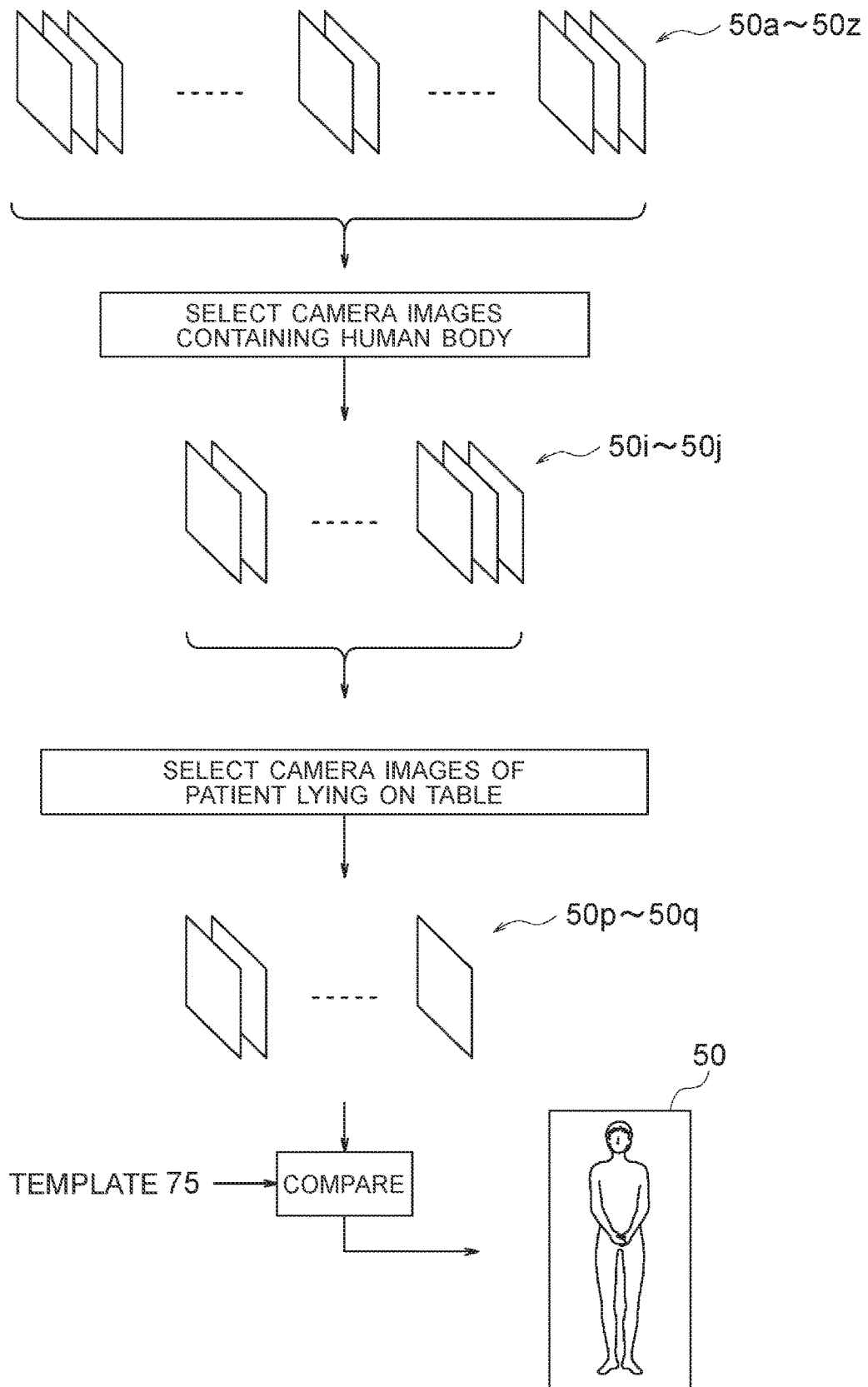
FIG. 10 is an explanatory diagram for an example of an identifying method of identifying a camera images 50.

Once Step ST21 has started, the processor in the processing apparatus 84 executes the processing for identifying a camera image 50 containing the patient 40 lying on the table 4 in the posture suitable for imaging from among the series of camera images produced by the camera-image producing section 800 (see FIG. 10).

FIG. 10 is an explanatory diagram for an example of an identifying method of identifying a camera image 50 containing the patient 40 lying on the table 4 in the posture suitable for imaging from among a series of camera images 50a to 50z produced by the camera-image producing section 800.

The processor in the processing apparatus 84 excludes camera images not containing a human body from among the series of camera images 50a to 50z, and selects camera images 50i to 50j containing a human body. Whether a camera image contains a human body or not can be decided using a known motion detection technique.

Next, the processor in the processing apparatus 84 selects camera images 50p to 50q of the patient 40 lying on the table 4 from among the selected camera images 50i to 50j. Whether the patient 40 is lying on the table 4 or not can be decided from a positional relationship between the table 4 and the detected human being, etc.

Finally, the processor in the processing apparatus 84 reads the template 75 (see FIG. 9) from the storage device 83. It then compares each of the plurality of selected camera images 50p to 50q with the template 75, and identifies a camera image 50 containing the patient 40 lying on the table 4 in the posture suitable for imaging from among the plurality of selected camera images 50p to 50q.

Since the patient 40 generally attempts to assume a comfortable posture after lying on the table 4, she or he makes fine adjustments of his or her posture on the table 4. In addition, the radiologic technologist 9 may sometimes help the patient 40 to achieve a posture suitable for imaging. Therefore, it is contemplated that the posture of the patient 40 is not constant and will change after the patient 40 has lain on the table 4. The template 75, however, represents a standard human posture in imaging. Thus, a camera image 50 containing the patient 40 lying on the table 4 in a posture suitable for imaging can be identified by detecting a camera image most similar to the template 75 from among the camera images 50p to 50q.

As a technique of comparing the camera images 50p to 50q with the template 75, an affine transformation, for example, may be employed. In the affine transformation, processing of enlarging, shrinking, and rotating one or both of the camera images 50p to 50q and template 75 can be performed, and therefore, the camera image 50 containing the patient 40 lying on the table 4 in the posture suitable for imaging can be identified from among the series of camera images 50p to 50q regardless of the body shape of the patient 40.

In the case that the radiologic technologist 9 stays near the table 4, it may be generally contemplated that she or he is making fine adjustments of the posture of the patient 40 while the patient 40 is lying on the table 4. Accordingly, the processor in the processing apparatus 84 decides whether or not there exist a plurality of human beings within the imaging field of view 61, and in the case that a plurality of human beings are detected in the camera image, the processor may decide that the patient 40 is yet to achieve the posture suitable for imaging. By making such a decision, the number of camera images among the series of camera images 50a to 50z that should be compared with the template 75 can be reduced, and thus, the time required for the comparison processing can be reduced.

Referring to Method 2, after the patient 40 has lain on the cradle 41, the radiologic technologist 9 confirms that the posture of the patient 40 is maintained in the posture suitable for imaging. Once the radiologic technologist 9 has confirmed this, a confirmation signal representing that the patient 40 is confirmed to assume the posture suitable for imaging is sent to the operator console 8. The confirmation signal can be sent to the operator console 8 by, for example, the radiologic technologist 9 pressing several kinds of buttons provided on the front side of the gantry 2, or performing required operations on the touch panel provided on the front side of the gantry 2. Once the processor in the processing apparatus 84 has received the confirmation signal, it puts a mark on a camera image among the series of camera images 50a to 50z that is acquired at a time point when the confirmation signal is received. Therefore, by detecting the marked camera image from among the series of camera images 50a to 50z, the processor in the processing apparatus 84 can identify the camera image 50 containing the patient 40 lying on the table 4 in the posture suitable for imaging.

Referring to Method 3, AI (Artificial Intelligence), such as deep learning or machine learning, is used to identify a camera image 50. When AI is used, the camera image 50 can be identified by, for example, the following learning step and inference step.

At the learning step is generated a model for identifying a camera image of the patient lying on the table in the posture suitable for imaging. The model can be generated by, for example, learning the following camera images (a) and (b):

(a) a camera image capturing a human being lying on the table in the posture suitable for imaging; and (b) a camera image capturing a human being lying on the table in a posture unsuitable for imaging.

The model obtained by learning the camera images (a) and (b) is stored in the storage device 83 or another storage device (X-ray CT apparatus-accessible storage device).

The inference step comprises: inputting the series of camera images 50a to 50z to the model obtained at the learning step, making an inference for identifying a camera image 50 containing the patient 40 lying on the table 4 in the posture suitable for imaging from among the series of camera images 50a to 50z, and outputting the camera image 50 as an output image. The inference may be executed by the processor included in the X-ray CT apparatus, or a processor included in a different apparatus (for example, a workstation connected to the X-ray CT apparatus via the communication network 12) from the X-ray CT apparatus.

After identifying the camera image 50, the flow goes to Step ST22.

At Step ST22, the processor in the processing apparatus 84 executes the processing of detecting a body part to be imaged of the patient 40 from within the camera image 50 identified at Step ST21. The processor in the processing apparatus 84 executes the processing of detecting the body part to be imaged by the detecting section 820 (see FIG. 6). For example, the body part to be imaged can be detected by identifying a body part of a human body that has a characteristic feature in shape and is easy to detect from within the camera image 50, and detecting the body part to be imaged with reference to the identified body part. In a human body, a shoulder part, for example, is an easily detectable body part because it has a characteristic feature in shape. Therefore, the shoulder part can be detected from the whole body of the patient 40, and the body part to be imaged can be identified with reference to the shoulder part. According to the present embodiment, the body part to be imaged is assumed to be a chest. Therefore, the shoulder part is identified from within the camera image 50, and the chest of the patient 40 can be detected based on information on the position of the shoulder part. After detecting the body part to be imaged, the flow goes to Step ST23.

Figure 11:
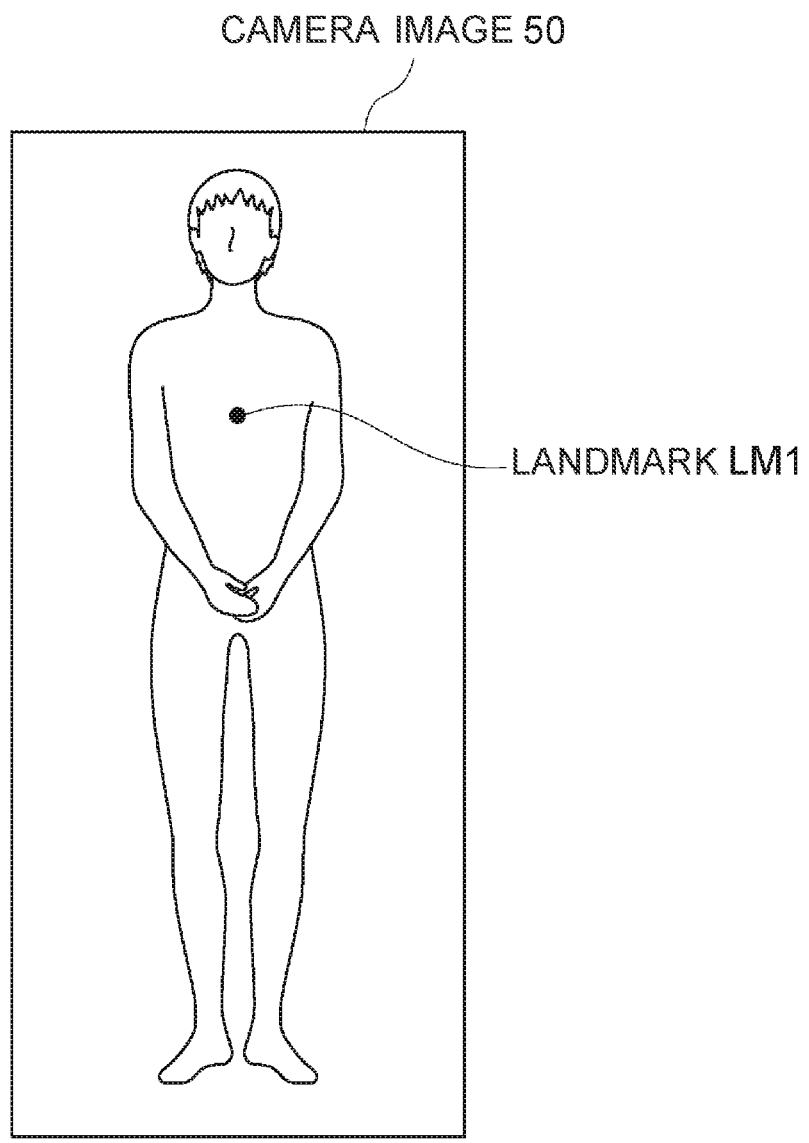
FIG. 11 is a diagram showing a landmark LM1 in a first examination.

At Step ST23, the processor in the processing apparatus 84 executes the processing of fixing a landmark with reference to the body part to be imaged in the camera image 50. The processor in the processing apparatus 84 executes the processing of fixing a landmark by the landmark fixing section 830 (see FIG. 6). FIG. 11 shows a fixed landmark LM1. The processor in the processing apparatus 84 can fix the landmark LM1 based on, for example, the size, position, shape, and/or the like of the body part to be imaged. According to the present embodiment, the body part to be imaged is the chest, and therefore, the processor in the processing apparatus 84 can fix the landmark LM1 based on the size, position, shape, and/or the like of the chest. The landmark LM1 may be fixed in, for example, the pit of the stomach or its proximity of the patient, although it may be fixed at a position away from the pit of the stomach or its proximity.

Returning to FIG. 7, the description will be continued.

Figure 12:
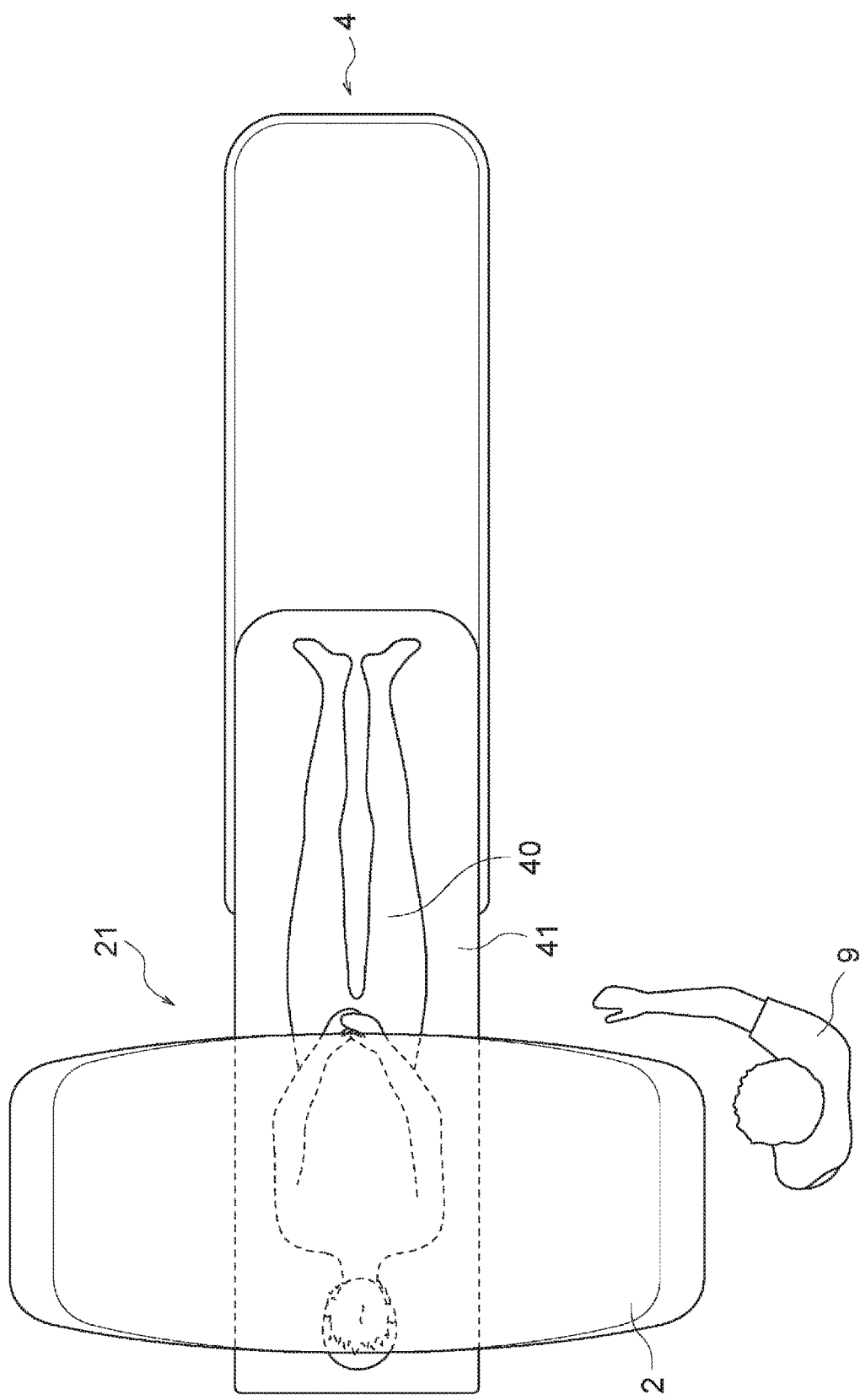
FIG. 12 is a diagram showing the table after moving the patient 40 into the bore 21.

After fixing the landmark LM1 at Step ST2, the flow goes to Step ST3. At Step ST3, the table 4 is driven to move the patient 40 into the bore 21 (see FIG. 12), and a scout scan is performed.

Here, the chest is assumed as the body part to be imaged of the patient 40. Therefore, the scout scan is performed on a body part including the chest of the patient 40. Data obtained by the scout scan is collected in the DAS 26 (see FIG. 5), and the collected data is sent to the operator console 8. In the operator console 8, the processor in the processing apparatus 84 executes the processing of image reconstruction based on the data obtained by the scout scan to reconstruct a scout image. The processor in the processing apparatus 84 executes the processing of reconstructing the scout image by the reconstructing section 840 (see FIG. 6). The radiologic technologist 9 can observe the reconstructed scout image on the display device 82.

Figure 13:
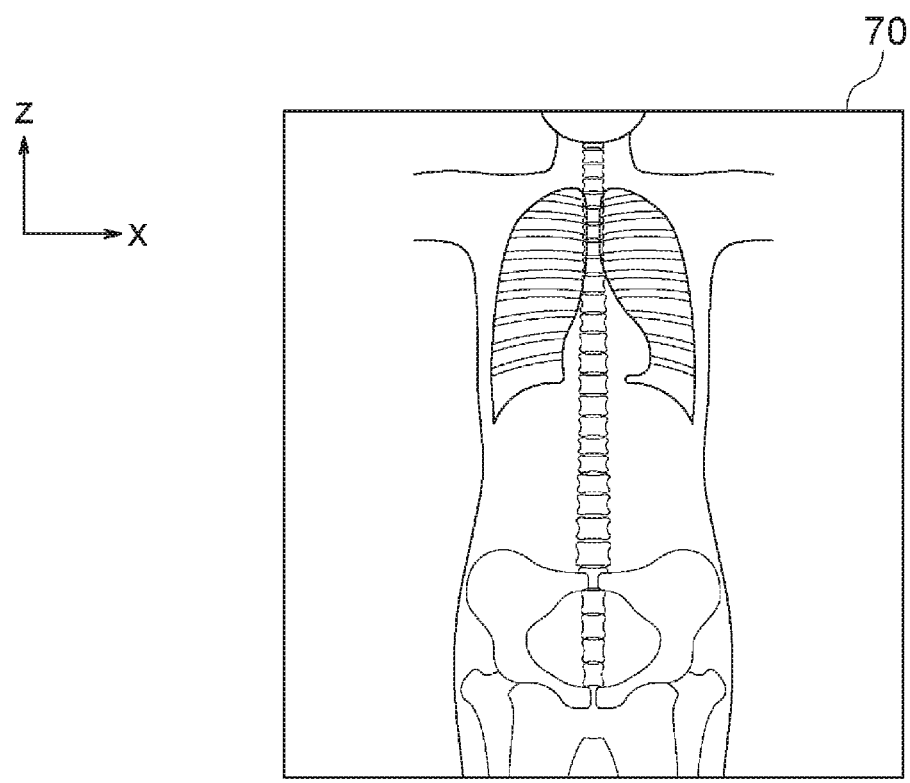
FIG. 13 is a diagram showing an example of a scout image.

FIG. 13 is a diagram showing an example of the scout image.

The scout scan can generally acquire scout images in an axial, sagittal, and coronal cross sections. In FIG. 13, a scout image 70 in the coronal cross section is shown as an example of the scout images. The scout image 70 is stored in the storage device 83 (see FIG. 5). After performing the scout scan, the flow goes to Step ST4.

Figure 14:
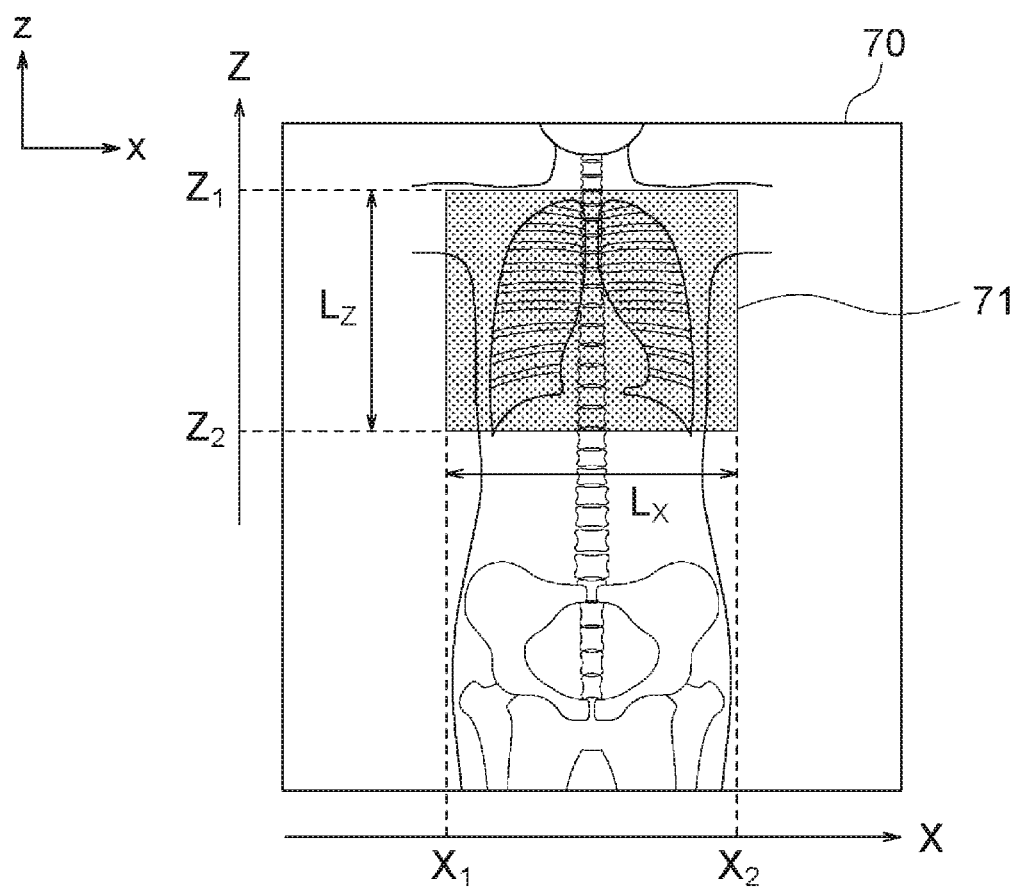
FIG. 14 is a diagram showing an example of an imaged range 71 in a main scan.

At Step ST4, an imaged range in a main scan is defined (see FIG. 14).

FIG. 14 is a diagram showing an example of the imaged range 71 in the main scan.

The processor in the processing apparatus 84 executes the processing for defining an imaged range. The processor in the processing apparatus 84 executes the processing of defining an imaged range by the imaged-range defining section 850 (see FIG. 6). Since according to the present embodiment, the object to be imaged is the chest, an operation for defining an imaged range to include the chest is performed. Specifically, the processing apparatus 84 defines an imaged range on the scout image 70 according to an amount of shift ($\Delta y$, $\Delta z$) of the table 4 (and cradle 41) from a home position, the height of the table 4 (cradle 41), and landmark data representing the landmark LM1. The landmark data may include, for example, position data representing the position of the landmark with respect to the patient (or the body part to be imaged of the patient), position data representing the position of the landmark relative to the cradle 41, etc.

After the imaged-range defining section 850 has defined the imaged range, the display device 82 displays the scout image 70, and the imaged range 71 positioned relative to the scout image 70, as shown in FIG. 14. Since according to the present embodiment, the body part to be imaged is the chest, the imaged range 71 is defined in the chest. The length Lx of the imaged range 71 in the x-direction and the length Lz thereof in the z-direction can be set based on, for example, the lengths of the body part to be imaged (the chest according to the present embodiment) of the patient 40 in the x- and z-directions, the height of the patient 40, or the like.

Moreover, in the storage device 83 are saved imaged-range data representing the imaged range 71 and landmark data representing the landmark LM1. The imaged-range data representing the imaged range 71 includes, for example, position data representing a position z1 of an upper end of the imaged range 71 in the z-direction, position data representing a position z2 of a lower end thereof in the z-direction, position data representing a position x1 of a right edge of the imaged range 71 in the x-direction, position data representing a position x2 of a left edge thereof in the x-direction, etc. The imaged-range data and landmark data are saved as position data whose reference position is at an origin of machine coordinates or an origin of human body coordinates. Furthermore, in the storage device 83 is stored position data representing the height of the table (cradle) in the scan. The position data representing the height of the table (cradle) may be stored as position data representing the position of the table (cradle) in the y-direction.

After defining the imaged range 71, the flow goes to Step ST5.

At Step ST5, a main scan for acquiring a CT image of the imaged range 71 is performed. After the main scan is completed, the flow goes to Step ST6.

At Step ST6, the radiologic technologist 9 performs an examination terminating operation. Once the examination terminating operation has been performed, several kinds of data to be sent to the PACS 11 are generated.

Figure 15:
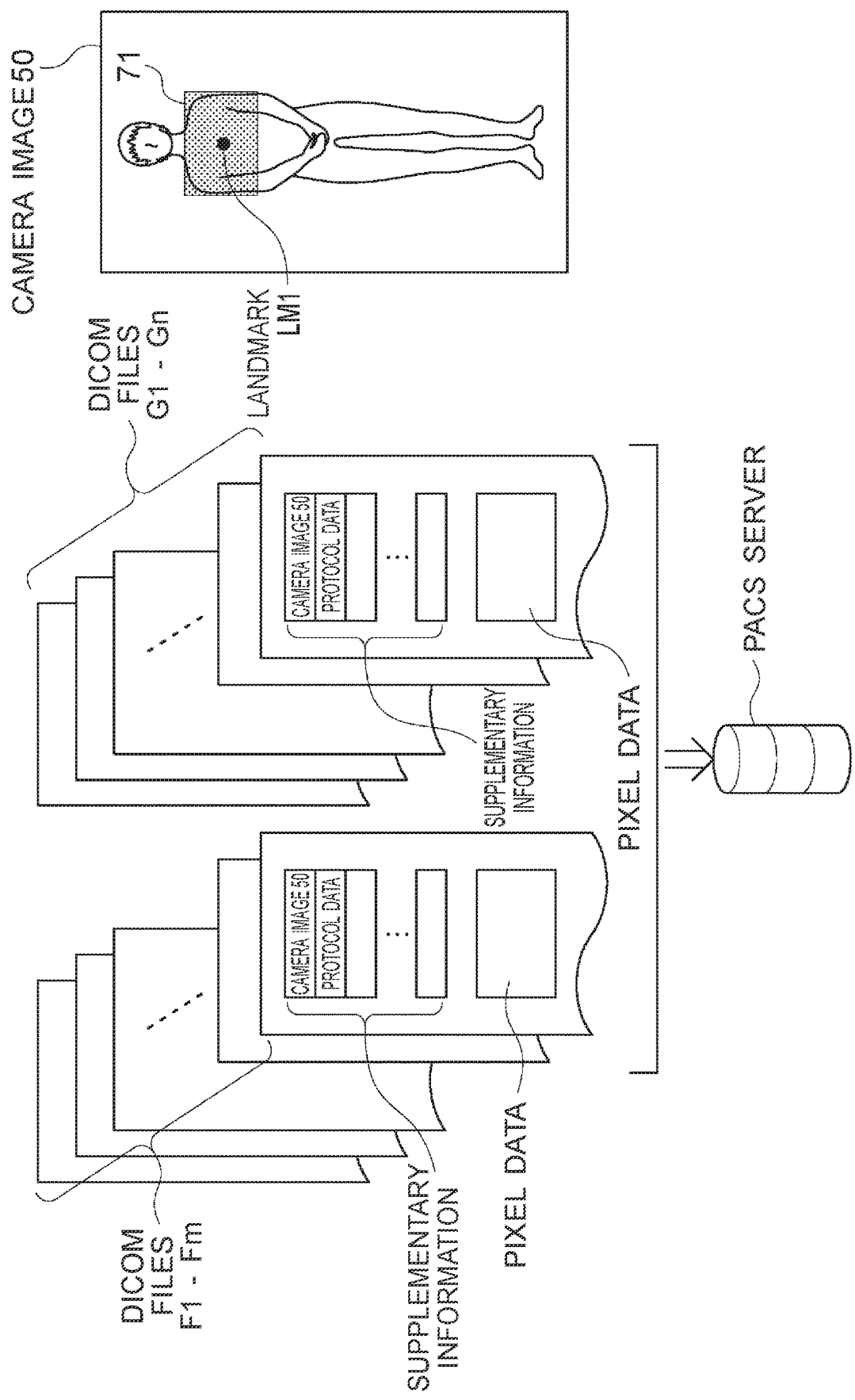
FIG. 15 is an explanatory diagram for an example of several kinds of data sent to a PACS 11.

FIG. 15 is an explanatory diagram for an example of several kinds of data sent to the PACS 11.

The X-ray CT apparatus creates DICOM files F1 to Fm and G1 to Gn.

The DICOM files F1 to Fm store therein a scout image acquired in the scout scan, while the DICOM files G1 to Gn store therein a CT image acquired in the main scan.

In the DICOM files F1 to Fm are stored pixel data for a scout image and supplementary information. In the DICOM files F1 to Fm, pixel data for a scout image in mutually different slices are stored.

In the DICOM files F1 to Fm are also stored medical patient information provided in an examination list, imaging condition information representing imaging conditions in the scout scan, etc., as data elements of the supplementary information. Moreover, in the DICOM files F1 to Fm are stored the camera image 50, protocol data, etc., as data elements of the supplementary information. The camera image 50 and protocol data are stored as data elements attached with a private tag. The protocol data includes landmark data representing the landmark LM1, imaged-range data representing the imaged range 71, etc.

On the other hand, in the DICOM files G1 to Gn are stored pixel data for a CT image acquired in the main scan and supplementary information. In the DICOM files G1 to Gn, pixel data for a CT image in mutually different slices are stored.

In the DICOM files G1 to Gn are also stored imaging condition information representing imaging conditions in the main scan, a dose index, medical patient information provided in the examination list, etc., as supplementary information. Similarly to the DICOM files F1 to Fm, in the DICOM files G1 to Gn are also stored the camera image 50 and protocol data as the supplementary information.

The X-ray CT apparatus 1 (see FIG. 2) sends the DICOM files F1 to Fm and G1 to Gn having the structures described above to the PACS 11 (see FIG. 1).

The radiologic technologist 9 tells the patient 40 that the examination is completed, and discharges the patient 40 from the table 4. In this way, the first examination of the patient 40 is completed.

Figure 7:
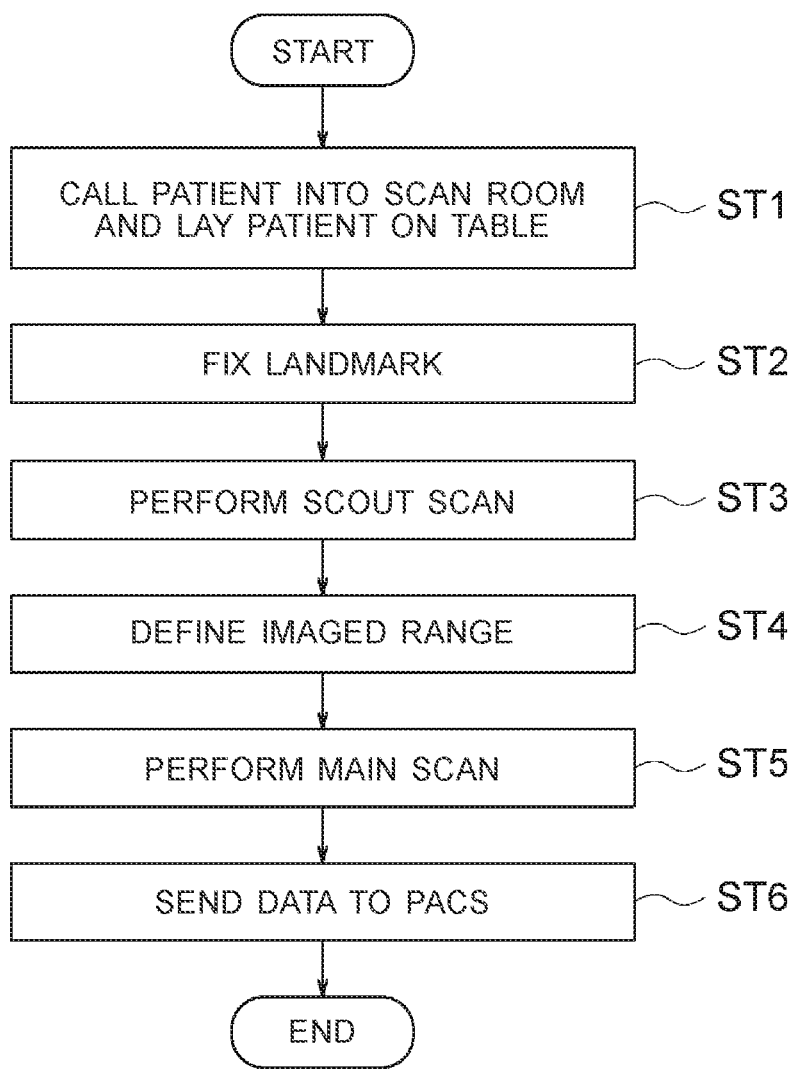
FIG. 7 is a flow chart in examining a patient.

Next, a case in which after a certain period of time has passed from the first examination, a follow-up examination of the patient 40 is performed will be described referring to the flow in FIG. 7.

Figure 16:
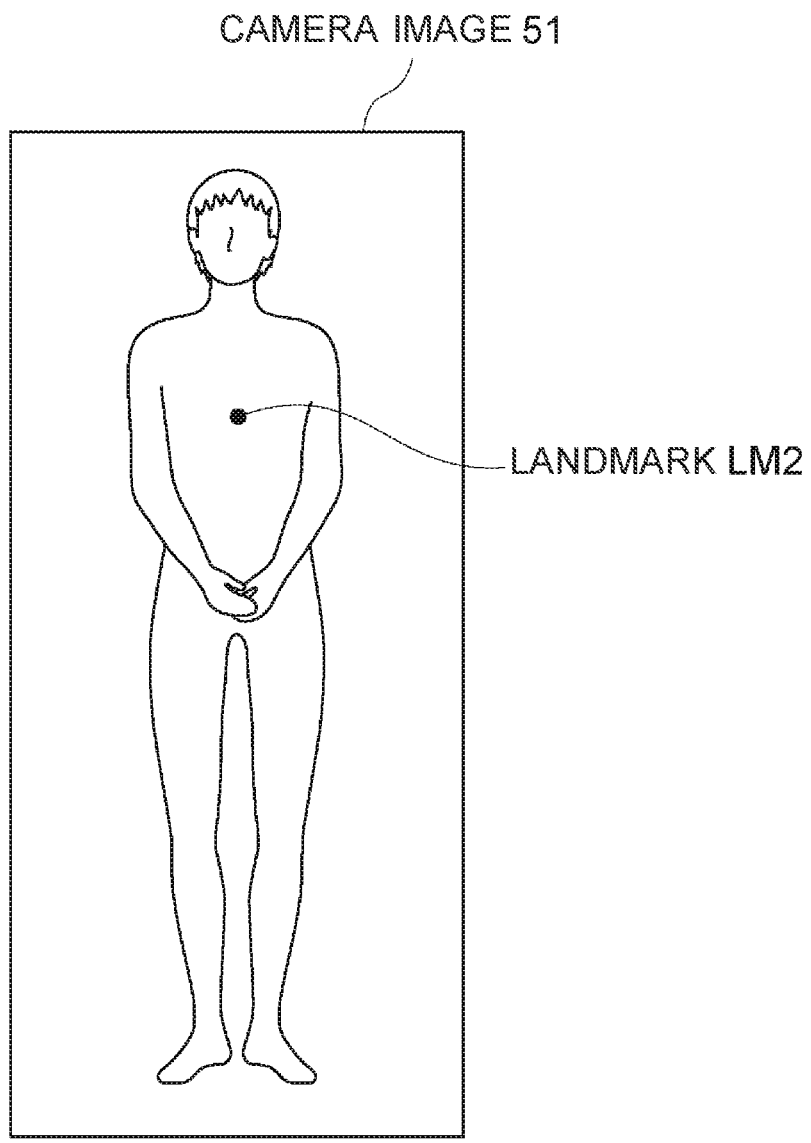
FIG. 16 is a diagram showing a landmark LM2 in a follow-up examination.

Referring to the follow-up examination, steps ST1 and ST2 are the same as imaging in the previous examination. Therefore, the patient 40 is laid on the table 4 and a landmark LM2 is fixed. The landmark LM2 is fixed following the flow shown in FIG. 8, as in the first examination. Therefore, a camera image of the patient lying on the table 40 in the posture suitable for imaging is identified from among a series of camera images of the patient 40 acquired in the follow-up examination (Step ST21), the chest, which is the body part to be imaged, is detected (Step ST22), and the landmark LM2 is fixed (Step ST23). FIG. 16 schematically shows a camera image 51 identified in the follow-up examination, and the landmark LM2 fixed then. The camera image 51, and landmark data representing the landmark LM2 are stored in the storage device 83.

Figure 17:
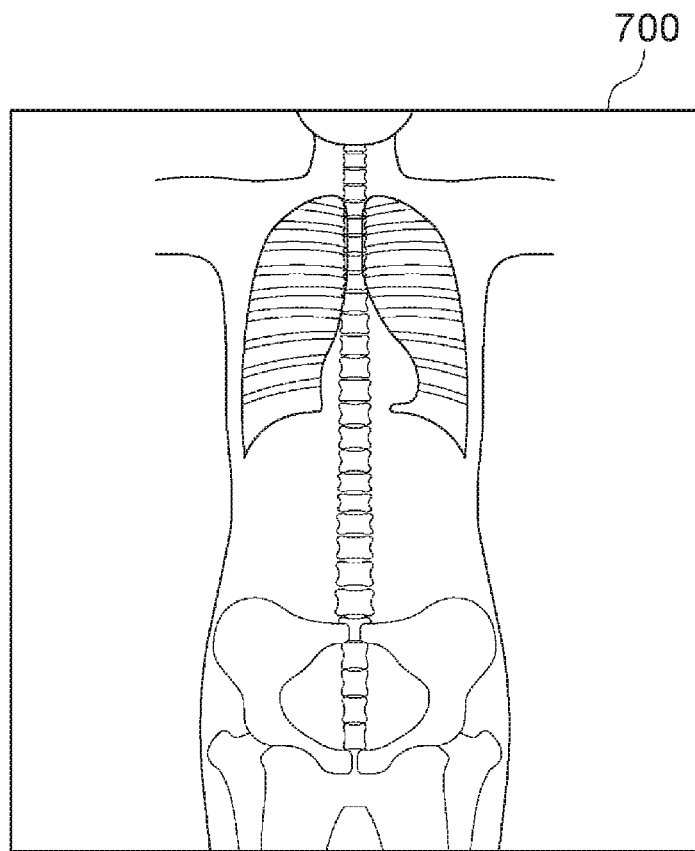
FIG. 17 is a diagram showing a scout image 700 in the follow-up examination.

At Step ST3, a scout scan is performed. By performing the scout scan, a scout image 700 in the follow-up examination is obtained, as shown in FIG. 17.

At Step ST4, processing of defining on the scout image 700 an imaged range in a main scan in the follow-up examination is executed. In the follow-up examination, an attempt is made to define the same imaged range as that in the first examination. Now a method of defining an imaged range in the main scan in the follow-up examination will be described referring to FIG. 18.

Figure 18:
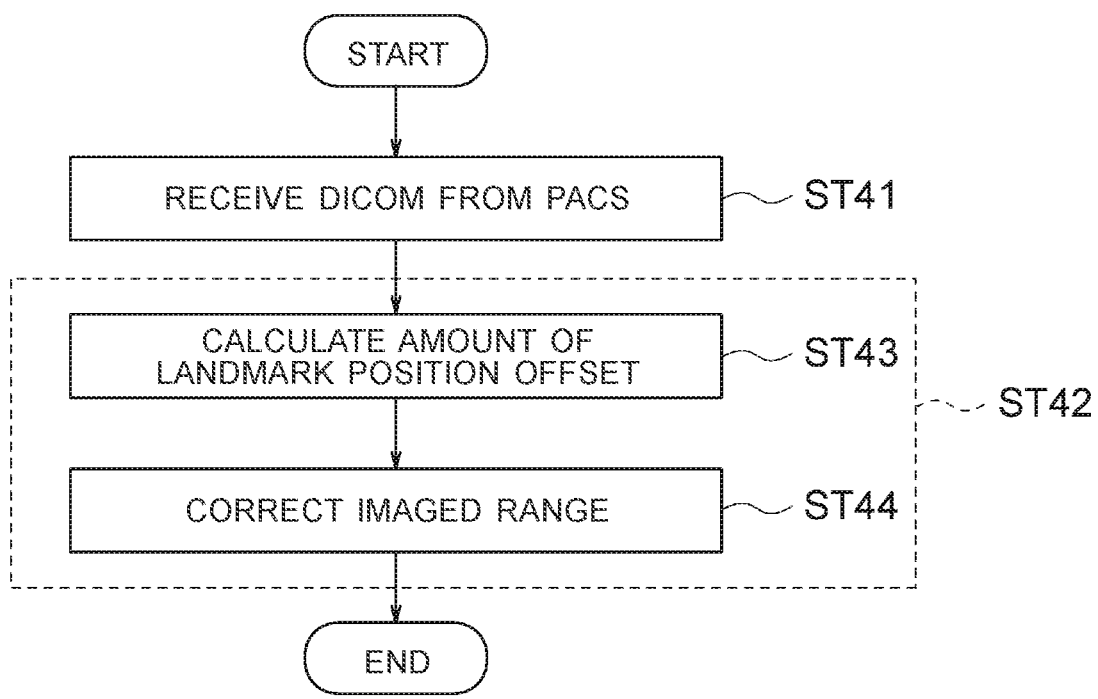
FIG. 18 is a chart showing flow of an example of a method of defining an imaged range in the follow-up examination.

FIG. 18 is a chart showing flow of an example of the method of defining an imaged range in the follow-up examination.

At Step ST41, a DICOM file (see FIG. 15) created in the first examination is received from the PACS 11. To receive the DICOM file, the radiologic technologist 9 uses the input device 81 to issue to the PACS 11 a request to transfer any one of the DICOM files F1 to Fm and G1 to Gn. On the receipt of the transfer request, the PACS 11 sends to the operator console 8 in the X-ray CT apparatus 1 the file for which the transfer request has been issued. Thus, the X-ray CT apparatus 1 can receive the DICOM file created in the first examination. In the received DICOM file are stored the landmark data representing the landmark LM1 and imaged-range data representing the imaged range 71 fixed/defined in the first examination, etc. (see FIG. 15). The received DICOM file is stored in the storage device 83. After receiving the DICOM file, the flow goes to Step ST42.

At Step ST42, the processor in the processing apparatus 84 executes the processing of defining an imaged range in the follow-up examination. The processor in the processing apparatus 84 executes the processing of defining an imaged range by the imaged-range defining section 850 (see FIG. 6). Step ST42 comprises Steps ST43 and ST44, which will be described in turn below.

Figure 19:
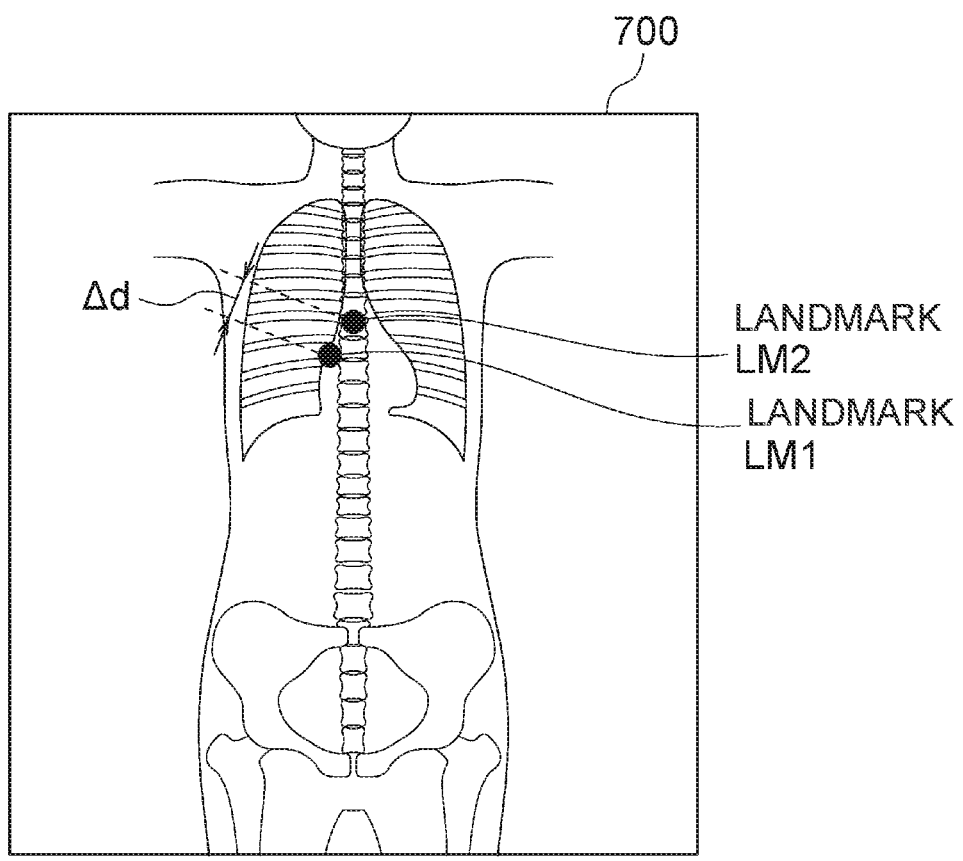
FIG. 19 is a diagram showing an amount Δd of position offset between the landmark LM1 in the first examination and the landmark LM2 in the follow-up examination.

At Step ST43, the processor in the processing apparatus 84 extracts the landmark data representing the landmark LM1 in the first examination included in the DICOM file received at Step ST41. The processor in the processing apparatus 84 also extracts the landmark data representing the landmark LM2 fixed in the follow-up examination from the storage device 83. The processor in the processing apparatus 84 then calculates an amount Δd of position offset between the landmarks LM1 and LM2 based on the landmark data representing the landmark LM1 in the first examination and that representing the landmark LM2 in the follow-up examination, as shown in FIG. 19.

Figure 20:
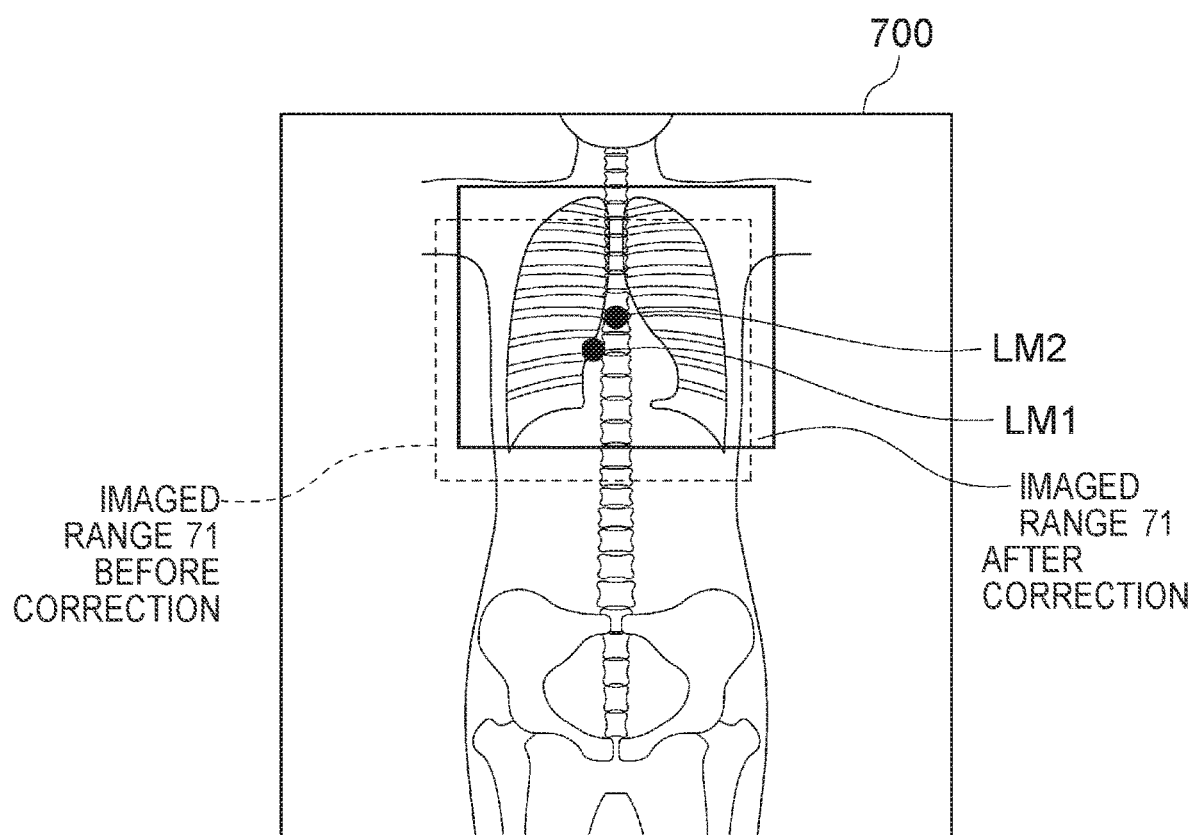
FIG. 20 is a diagram showing an imaged range after correcting the imaged range in the first examination.

At Step ST44, the processor in the processing apparatus 84 corrects the imaged-range data representing the imaged range 71 in the first examination based on the amount Δd of position offset calculated at Step ST43. By this correction, an imaged range can be positioned at the chest of the patient 40 in the follow-up scout scan, as shown in FIG. 20. In FIG. 20, the imaged range 71 before correcting the imaged-range data is indicated by a dashed line, and that after correcting the imaged-range data is indicated by a solid line.

The thus-corrected imaged range 71 is defined as the imaged range in the follow-up examination.

Figure 21:
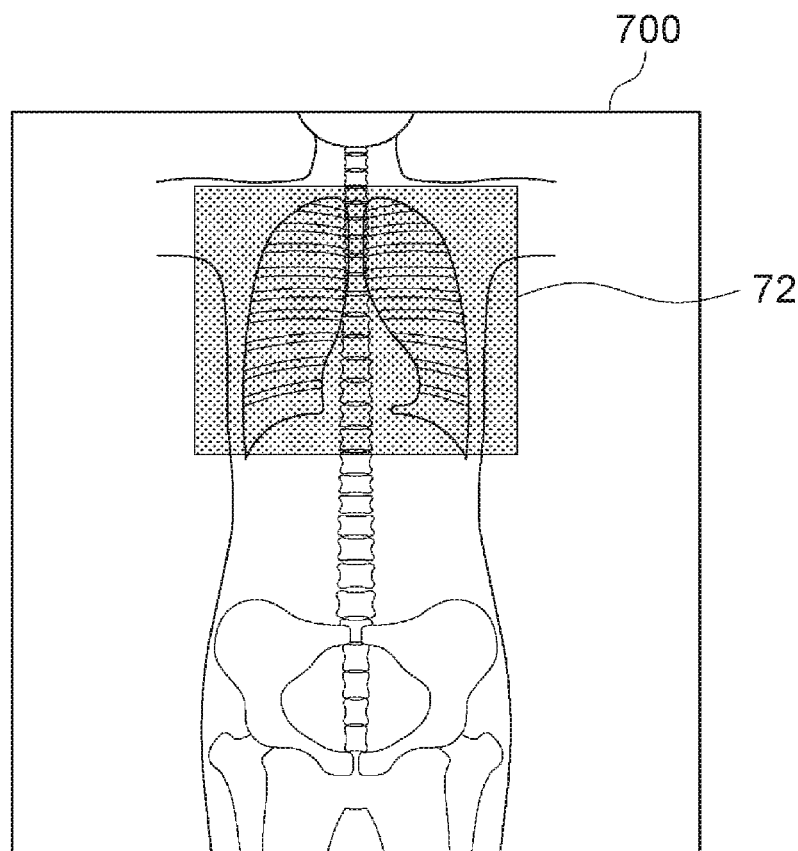
FIG. 21 is a diagram showing an imaged range 72 in the current follow-up examination displayed over the scout image 700.

The processor in the processing apparatus 84 instructs the display device 82 to display the corrected imaged range 71 as the imaged range in the follow-up examination. In response to the instructions, the display device 82 displays the imaged range in the current follow-up examination over the scout image 700. FIG. 21 shows the imaged range 72 in the current follow-up examination displayed over the scout image 700.

The imaged range 72 is displayed over the scout image 700. The radiologic technologist 9 decides whether or not the imaged range 72 in the current follow-up examination displayed over the scout image 700 is substantially the same as the imaged range 71 in the first examination. In the case that the imaged range 72 displayed over the scout image 700 is defined in the chest of the patient 40 similarly to the imaged range 71 in the first examination, the radiologic technologist 9 decides to perform the current follow-up examination with the imaged range 72 displayed over the scout image 700.

On the other hand, in the case that the radiologic technologist 9 decides that the imaged range 72 displayed over the scout image 700 is offset from the chest, she or he uses the input device 81 to perform an operation of modifying the imaged range 72. When it is desired to shift the position of the imaged range 72, for example, the radiologic technologist 9 can shift the imaged range 72 to a desired position by moving a cursor into the imaged range 72 and dragging the mouse. When it is desired to adjust the longitudinal or transverse length of the imaged range 72, for example, the radiologic technologist 9 can adjust the length of the imaged range 72 by moving the cursor onto a borderline delineating the imaged range 72 and dragging the mouse. —When the radiologic technologist has performed the operation of imaged range modification, the imaged-range defining section 850 defines the modified imaged range as the imaged range in the follow-up examination.

In this way, the imaged range 72 in the follow-up examination is defined on the scout image 700, and the flow shown in FIG. 18 ends.

Returning to FIG. 7, the description will be continued.

Once the imaged range 72 in the follow-up examination has been defined at Step ST4, the flow goes to Step ST5.

At Step ST5, a main scan for acquiring a CT image of the imaged range 72 is performed. After completing the main scan, the flow goes to Step ST6, and DICOM files for the current follow-up imaging are created for sending to the PACS 11; the flow then ends.

According to the present embodiment, the X-ray CT apparatus 1 comprises the camera 6, which has been acquiring a camera image of the imaging field of view 61 including the table 4 and its surroundings since before the patient 40 enters the scan room 100. In the first examination of the patient 40, the X-ray CT apparatus 1 identifies a camera image 50 containing the patient 40 lying on the table 4 in a posture suitable for imaging from among the series of camera images 50a to 50z captured by the camera 6. The X-ray CT apparatus 1 then stores the camera image 50, landmark, imaged range, etc., in DICOM files, and sends them to the PACS 11. The PACS 11 saves the DICOM files in the server. In the case that a follow-up examination of the patient 40 is performed at some later date, a landmark LM2 (see FIG. 16) is fixed, and data of the landmark LM1 and imaged range 71 in the first examination are extracted from a DICOM file saved in the PACS 11. Then, based on the landmarks LM1 and LM2 and imaged range 71, an imaged range 72 in the follow-up examination is defined. Since substantially the same range as the imaged range 71 in the first examination can thus be defined as the imaged range 72 in the follow-up examination, the imaged range in the past can be reproduced with good precision to enhance reliability of subsequent observation of the patient's condition.

Moreover, according to the present embodiment, the imaged-range defining section 850 defines the imaged range 72 in the follow-up examination based on the landmarks LM1 and LM2 and previous imaged range 71. Since work required for the radiologic technologist 9 to define the imaged range 72 can thus be simplified, stress in the work of the radiologic technologist 9 can be mitigated.

Furthermore, according to the present embodiment, the camera image 50 and protocol data are stored in each of the DICOM files F1 to Fm and G1 to Gn as supplementary information for the scout image acquired in the scout scan (and for the CT image acquired in the main scan), as shown in FIG. 15. Therefore, the radiologic technologist 9 can get the imaged-range data representing the imaged range in the first examination by merely receiving one of the DICOM files F1 to Fm and G1 to Gn from the PACS 11. Since it is thus unnecessary for the radiologic technologist 9 to perform work of searching for a file in which the imaged-range data representing the imaged range 71 in the first examination is stored from among the DICOM files F1 to Fm and G1 to Gn, stress in the work of the radiologic technologist 9 can be mitigated. On the other hand, it is possible to store the camera image 50 in a DICOM file separate from the DICOM files F1 to Fm and G1 to Gn (see FIG. 22).

Figure 22:
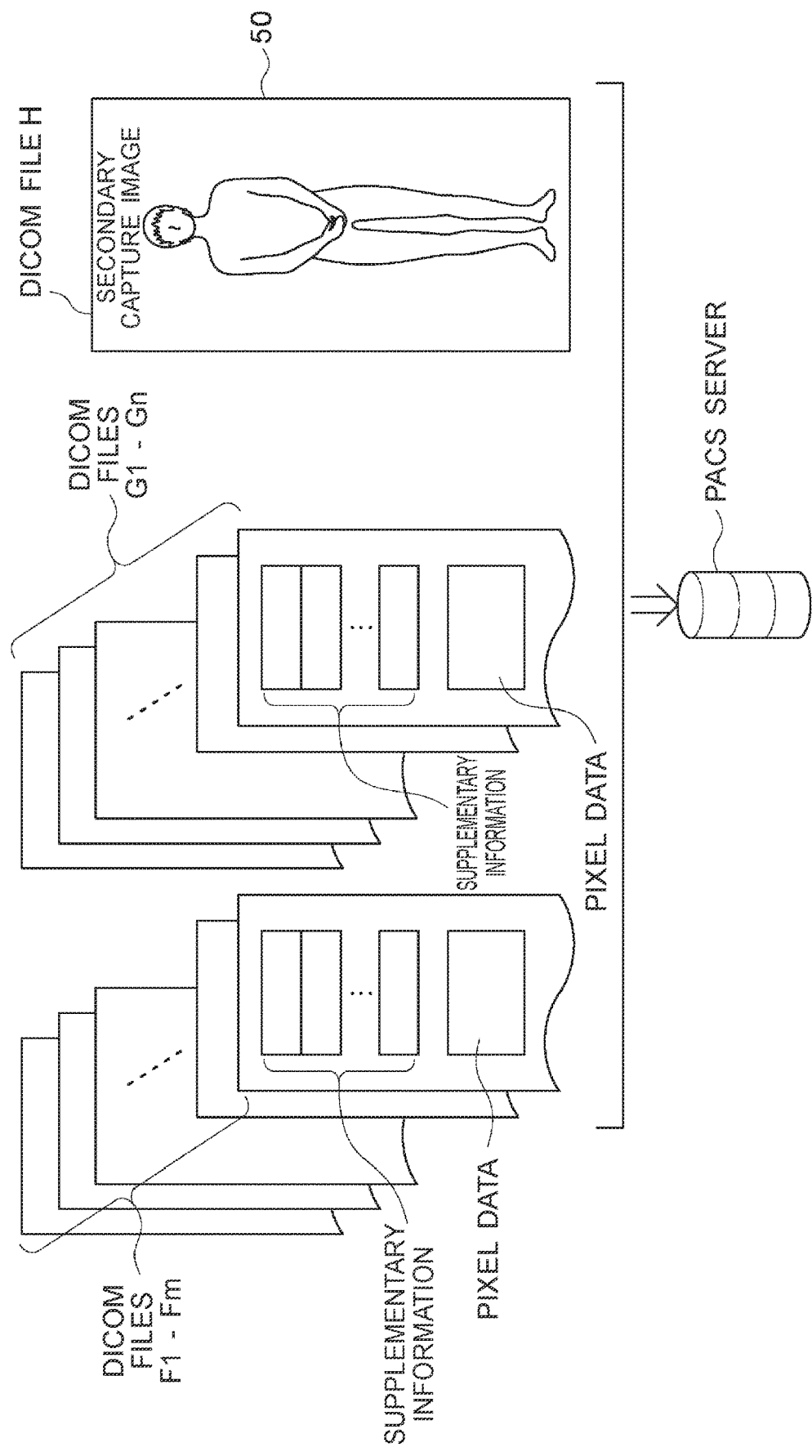
FIG. 22 is an explanatory diagram for an example in which a camera image 50 is stored in a DICOM file separate from DICOM files F1 to Fm and G1 to Gn.

FIG. 22 is an explanatory diagram for an example in which the camera image 50 is stored in a DICOM file separate from the DICOM files F1 to Fm and G1 to Gn.

In FIG. 22, the camera image 50 is stored in another DICOM file H as "Secondary Capture Image." Therefore, the camera image 50 is managed in the DICOM file H separate from the DICOM files F1 to Fm and G1 to Gn.

Since it is unnecessary to store the camera image 50 in each of the DICOM files F1 to Fm and G1 to Gn in FIG. 22, it is possible to reduce the file sizes of the DICOM files F1 to Fm and G1 to Gn.

Figure 23:
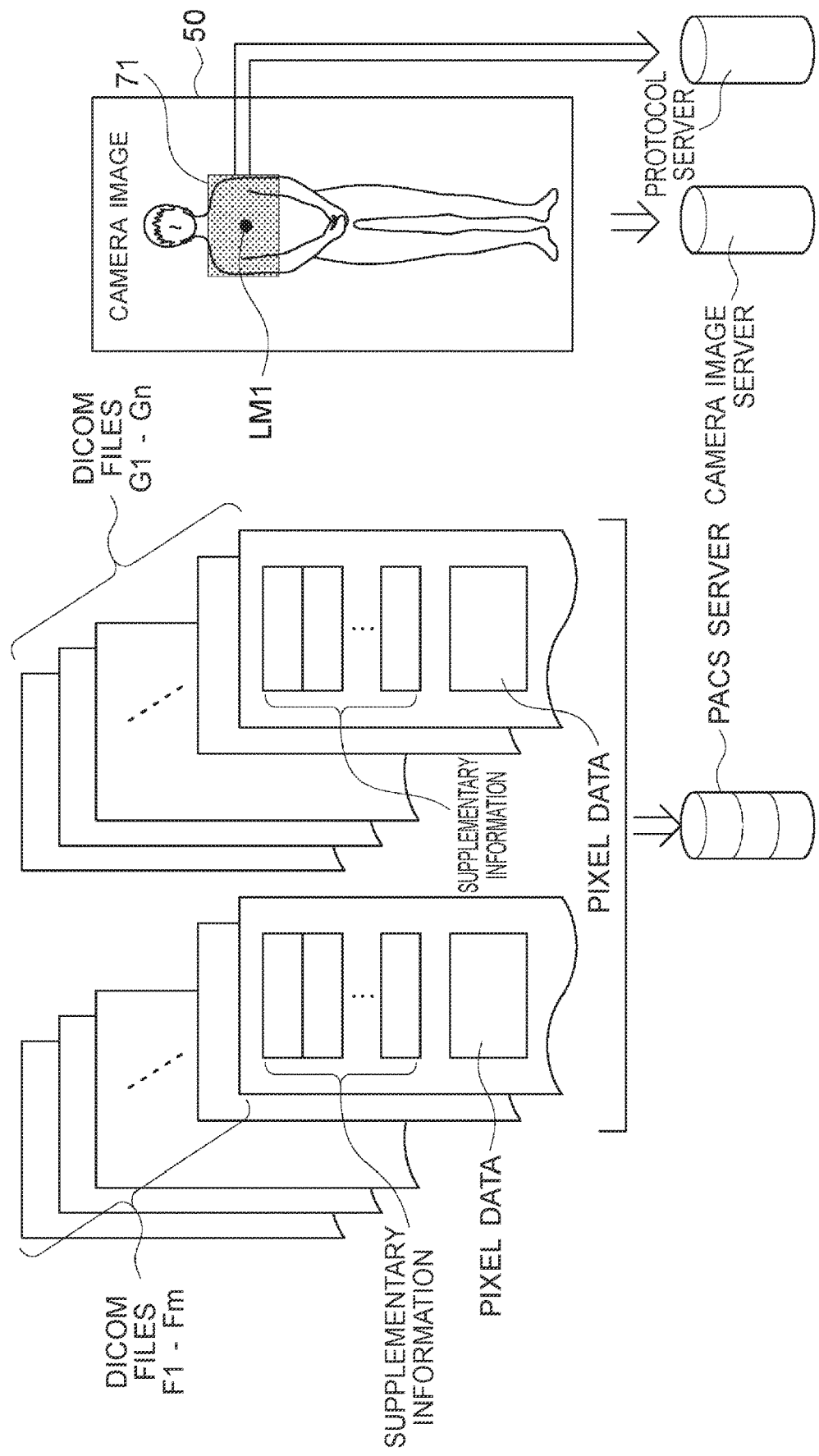
FIG. 23 is a diagram showing a case in which the camera image 50 and protocol data are saved in other servers.

Moreover, rather than saving the camera image 50 and protocol data in the server of the PACS 11, they may be saved in servers separate from that of the PACS 11 (see FIG. 23).

FIG. 23 is a diagram showing a case in which the camera image 50 and protocol data are saved in other servers.

FIG. 23 shows a camera image server and a protocol server, in addition to the server of the PACS 11. The camera image server saves camera images, while the protocol server saves protocol data, such as the imaged range 71 and landmark LM1. The camera image server and protocol server may be provided in a medical institution, such as a hospital, that owns the X-ray CT apparatus 1, separate from the server of the PACS 11. The camera image saved in the camera image server, and the protocol data saved in the protocol server are associated with the data saved in the PACS 11 via an identification number. By such association via the identification number, a camera image 50 and protocol data corresponding to the data saved in the server of the PACS 11 can be easily identified from the identification number when they are saved in a server(s) separate from the server of the PACS 11.

According to the present embodiment, the camera 6 is attached to the ceiling 101. A location at which the camera 6 is installed is, however, not limited to the ceiling 101, and it may be installed in a location, such as a side wall of the scan room 100, different from the ceiling 101 insofar as a camera image suitable for positioning the imaged range with respect to the patient 40 can be acquired. Moreover, it is possible to attach the camera 6 onto the gantry 2, rather than to the ceiling 101 or side wall of the scan room 100.

According to the present embodiment, the landmark and imaged range are fixed/defined based on a camera image containing the whole body of the patient 40. However, a camera image containing only a body part to be imaged and its surrounding body parts of the patient 40, instead of the whole body of the patient 40, may be acquired, and the landmark and imaged range may be fixed/defined for the body parts of the patient 40 contained in the camera image.

The present embodiment addresses a case in which the imaged range 72 in the current (second) examination is defined based on the landmark data representing the landmark LM1 and imaged-range data representing the imaged range 71 in the previous (first) examination. The present disclosure is, however, not limited to the embodiment, and it may be applied to any case, such as a follow-up examination, in which an examination is desired to be performed on the same imaged range as that defined in an examination in the past. For example, in the case that a number of examinations were performed in the past, an imaged range in a current examination can be defined based on the landmark data representing the landmark and imaged-range data of the imaged range in any one of the number of examinations.

In the present embodiment, the methods of defining an imaged range in the patient 40 are described taking the X-ray CT apparatus 1 as the medical apparatus. The medical apparatus in the present disclosure is, however, not limited to the X-ray CT apparatus, and may be applied to any medical apparatus (for example, an MRI apparatus, a PET-CT apparatus, or a PET-MR apparatus) in which it is necessary to perform an examination that acquires a medical image of the patient 40 in the same imaged range as that in past imaging.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present disclosure. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

The invention claimed is:

1. An imaged-range defining apparatus of a medical apparatus for acquiring a medical image of a patient, the imaged-range defining apparatus comprising:
   a camera-image producing section for producing a first camera image containing an external appearance of the patient lying on a table in a first examination of the patient;
   a landmark fixing section for fixing a first landmark with reference to a body part to be imaged of the patient contained in the first camera image; and
   an imaged-range defining section for defining a first imaged range in the patient in a first scan performed in the first examination based on first landmark data representing the first landmark, wherein
   the camera-image producing section produces a second camera image containing the external appearance of the patient lying on a table in a second examination performed after the first examination,
   the landmark fixing section fixes a second landmark with reference to the body part to be imaged of the patient contained in the second camera image, and
   the imaged-range defining section defines a second imaged range in the patient in a second scan performed in the second examination based on the first landmark data, second landmark data representing the second landmark, and imaged-range data representing the first imaged range.

2. The imaged-range defining apparatus as recited in claim 1, wherein the imaged-range defining section calculates an amount of position offset between the first landmark and the second landmark, and defines the second imaged range based on the amount of position offset and imaged-range data representing the first imaged range.

3. The imaged-range defining apparatus as recited in claim 2, wherein the imaged-range defining section corrects the imaged-range data representing the first imaged range based on the amount of position offset, and defines as the second imaged range the first imaged range for which the imaged-range data has been corrected.

4. The imaged-range defining apparatus as recited in claim 1, further comprising an identifying section for identifying the first camera image from among a first series of camera images produced by the camera-image producing section in the first examination.

5. The imaged-range defining apparatus as recited in claim 4, wherein the identifying section identifies as the first camera image a camera image containing the patient lying on the table in a predetermined posture from among the first series of camera images.

6. The imaged-range defining apparatus as recited in claim 5, wherein the identifying section identifies the second camera image from among a second series of camera images produced by the camera-image producing section in the second examination.

7. The imaged-range defining apparatus as recited in claim 6, wherein the identifying section identifies as the second camera image a camera image containing the patient lying on the table in the predetermined posture from among the second series of camera images.

8. The imaged-range defining apparatus as recited in claim 1, wherein the first camera image is stored in a file as supplementary information for a medical image acquired in a scan in the first examination.

9. The imaged-range defining apparatus as recited in claim 1, wherein the first camera image is stored in a file separate from that in which the medical image acquired in the scan in the first examination is stored.

10. A medical apparatus for acquiring a medical image of a patient, comprising:
    a camera-image producing section for producing a first camera image containing an external appearance of the patient lying on a table in a first examination of the patient;
    a landmark fixing section for fixing a first landmark with reference to a body part to be imaged of the patient contained in the first camera image; and
    an imaged-range defining section for defining a first imaged range in the patient in a first scan performed in the first examination based on first landmark data representing the first landmark, wherein
    the camera-image producing section produces a second camera image containing the external appearance of the patient lying on a table in a second examination performed after the first examination,
    the landmark fixing section fixes a second landmark with reference to the body part to be imaged of the patient contained in the second camera image, and
    the imaged-range defining section defines a second imaged range in the patient in a second scan performed in the second examination based on the first landmark data, second landmark data representing the second landmark, and imaged-range data representing the first imaged range.

11. A computer-readable recording medium in which one or more processor-executable instructions are stored, the one or more instructions causing, when executed by the processor, the processor to execute an operation comprising the steps of:

producing a first camera image containing an external appearance of the patient lying on a table in a first examination of the patient;

fixing a first landmark with reference to a body part to be imaged of the patient contained in the first camera image;

defining a first imaged range in the patient in a first scan performed in the first examination based on first landmark data representing the first landmark;

producing a second camera image containing the external appearance of the patient lying on a table in a second examination performed after the first examination;

fixing a second landmark with reference to the body part to be imaged of the patient contained in the second camera image; and defining a second imaged range in the patient in a second scan performed in the second examination based on the first landmark data, second landmark data representing the second landmark, and imaged-range data representing the first imaged range.

* * * * *